(12) United States Patent
Samain et al.

(10) Patent No.: US 11,064,789 B2
(45) Date of Patent: Jul. 20, 2021

(54) COSMETIC TREATMENT OF KERATIN FIBRES

(71) Applicant: L'OREAL, Paris (FR)

(72) Inventors: Henri Samain, Bievres (FR); Franck Giron, Lagny sur Marne (FR); Nathalie Jager Lezer, Verrieres-le-Buisson (FR)

(73) Assignee: L'OREAL, Paris (FR)

( * ) Notice: Subject to any disclaimer, the term of this patent is extended or adjusted under 35 U.S.C. 154(b) by 400 days.

(21) Appl. No.: 15/315,130

(22) PCT Filed: May 29, 2015

(86) PCT No.: PCT/IB2015/054054
§ 371 (c)(1),
(2) Date: Nov. 30, 2016

(87) PCT Pub. No.: WO2015/181785
PCT Pub. Date: Dec. 3, 2015

(65) Prior Publication Data
US 2017/0215554 A1    Aug. 3, 2017

(30) Foreign Application Priority Data

May 30, 2014 (FR) ...................................... 1454908

(51) Int. Cl.
*A45D 40/26* (2006.01)
*A45D 2/48* (2006.01)
(Continued)

(52) U.S. Cl.
CPC ............... *A45D 40/26* (2013.01); *A41G 5/02* (2013.01); *A45D 2/48* (2013.01); *A61K 8/19* (2013.01);
(Continued)

(58) Field of Classification Search
CPC .......... A45D 40/26; A45D 2/48; A45D 40/00; A45D 2200/157; A45D 2200/205;
(Continued)

(56) References Cited

U.S. PATENT DOCUMENTS 1,527,964 A    2/1925 Gerardo Patino Jorge
2,323,595 A    7/1943 Hanisch
(Continued)

FOREIGN PATENT DOCUMENTS

CN    1416756 A    5/2003
CN    1541593 A    11/2004
(Continued)

OTHER PUBLICATIONS

Sep. 8, 2015 International Search Report issued in International Patent Application No. PCT/IB2015/054054.
(Continued)

*Primary Examiner* — Nahida Sultana
(74) *Attorney, Agent, or Firm* — Oliff PLC

(57) ABSTRACT

The present invention is directed towards a cosmetic assembly, of use for the treatment of keratin fibres, comprising a cosmetic composition having a melting point of between 40° C. and 120° C., and comprising at least 15% by weight of meltable compound(s), relative to the total weight of the composition; and a device (1) comprising a mould (2), the mould (2) comprising at least one cavity (5), into which or each of which at least one of said fibres can be at least partially introduced, for the purposes of moulding said composition onto at least one part of said fibre(s) present in the cavity or cavities (5). The present invention is also directed towards a process for cosmetic treatment of one or more keratin fibres.

23 Claims, 6 Drawing Sheets

(51) Int. Cl.
| | | |
|---|---|---|
| *A61K 8/92* | (2006.01) | |
| *A61K 8/19* | (2006.01) | |
| *A61K 8/81* | (2006.01) | |
| *A61Q 1/10* | (2006.01) | |
| *A41G 5/02* | (2006.01) | |
| *A61K 8/31* | (2006.01) | |
| *A45D 40/00* | (2006.01) | |

(52) U.S. Cl.
CPC .............. *A61K 8/31* (2013.01); *A61K 8/8111* (2013.01); *A61K 8/8141* (2013.01); *A61K 8/927* (2013.01); *A61Q 1/10* (2013.01); *A45D 40/00* (2013.01); *A45D 2200/157* (2013.01); *A45D 2200/205* (2013.01); *A61K 2800/31* (2013.01); *A61K 2800/43* (2013.01); *A61K 2800/87* (2013.01)

(58) Field of Classification Search
CPC .......... A41G 5/02; A61K 8/31; A61K 8/8141; A61K 8/8111; A61K 8/927; A61K 8/19; A61K 2800/31; A61K 2800/87; A61K 2800/43; A61Q 1/10
See application file for complete search history.

(56) References Cited

U.S. PATENT DOCUMENTS

| | | | |
|---|---|---|---|
| 2,421,432 A | 6/1947 | Phillips | |
| 3,559,657 A | 2/1971 | Bau | |
| 5,156,911 A | 10/1992 | Stewart | |
| 5,188,899 A | 2/1993 | Matsumoto et al. | |
| 5,307,826 A | 5/1994 | Iosilevich | |
| 5,706,634 A * | 1/1998 | Edwards | B29D 11/0024 53/239 |
| 5,944,028 A | 8/1999 | Gebhard | |
| 6,220,252 B1 | 4/2001 | Heintz | |
| 6,274,131 B1 | 8/2001 | Piot et al. | |
| 6,325,071 B1 | 12/2001 | Butcher | |
| 6,789,551 B2 | 9/2004 | Iosilevich | |
| 7,055,529 B2 | 6/2006 | Muraki et al. | |
| 7,083,347 B2 | 8/2006 | Marcotte et al. | |
| 7,347,993 B2 | 3/2008 | Bracken et al. | |
| 7,640,938 B2 | 1/2010 | Okajima et al. | |
| 9,937,640 B2 * | 4/2018 | Gibson | B29C 33/20 |
| 10,137,612 B2 * | 11/2018 | Gibson | B29C 33/44 |
| 2002/0189628 A1 | 12/2002 | Iosilevich | |
| 2003/0068344 A1 | 4/2003 | Ferrari et al. | |
| 2003/0185774 A1 | 10/2003 | Dobbs et al. | |
| 2004/0011372 A1 | 1/2004 | Park | |
| 2005/0031400 A1 | 2/2005 | Marcotte et al. | |
| 2005/0175648 A1 | 8/2005 | De La Poterie et al. | |
| 2007/0000511 A1 | 1/2007 | Okajima et al. | |
| 2007/0286831 A1 | 12/2007 | Kamada et al. | |
| 2008/0000491 A1 * | 1/2008 | Bodelin | A45D 34/042 132/200 |
| 2008/0006287 A1 | 1/2008 | Gueret | |
| 2008/0017215 A1 | 1/2008 | Thiebaut | |
| 2008/0286030 A1 | 11/2008 | Roder | |
| 2009/0217939 A1 | 9/2009 | Rabe et al. | |
| 2009/0223534 A1 | 9/2009 | Green | |
| 2010/0021406 A1 | 1/2010 | Raineau et al. | |
| 2010/0080766 A1 | 4/2010 | Dumousseaux et al. | |
| 2010/0095975 A1 | 4/2010 | Kim | |
| 2010/0119467 A1 | 5/2010 | Dumousseaux et al. | |
| 2010/0146710 A1 * | 6/2010 | Emmerling | A61K 8/447 8/107 |
| 2010/0221294 A1 * | 9/2010 | Kurek | A61K 8/987 424/401 |
| 2010/0254929 A1 | 10/2010 | Raineau | |
| 2011/0226414 A1 | 9/2011 | Guilhem | |
| 2012/0160258 A1 | 6/2012 | Cruz et al. | |
| 2013/0074865 A1 | 3/2013 | Santillan | |
| 2013/0081646 A1 | 4/2013 | Lamartine et al. | |
| 2013/0098387 A1 | 4/2013 | Shimizu et al. | |
| 2013/0114989 A1 * | 5/2013 | McNamara | A45D 40/265 401/130 |
| 2013/0152960 A1 | 6/2013 | Pays et al. | |
| 2013/0291320 A1 * | 11/2013 | Kirchhofer | A46D 3/005 15/22.1 |
| 2014/0105942 A1 | 4/2014 | Pistorio et al. | |
| 2014/0147547 A1 * | 5/2014 | Ueno | B29C 45/4421 425/556 |
| 2014/0290689 A1 | 10/2014 | Sutton et al. | |
| 2014/0291891 A1 * | 10/2014 | Charnay | A46B 9/021 264/296 |
| 2014/0314463 A1 | 10/2014 | Tranchant et al. | |
| 2014/0332026 A1 | 11/2014 | Peters et al. | |
| 2014/0339395 A1 * | 11/2014 | Kumpf | A46B 9/04 249/177 |
| 2015/0296953 A1 | 10/2015 | Murdock et al. | |
| 2016/0007711 A1 | 1/2016 | Bremner | |
| 2016/0058087 A1 | 3/2016 | Jang et al. | |
| 2016/0263010 A1 * | 9/2016 | Abdo | A61K 8/042 |
| 2017/0258700 A1 * | 9/2017 | Kang | C08G 18/3206 |
| 2018/0049531 A1 | 2/2018 | Leseman et al. | |
| 2018/0360703 A1 * | 12/2018 | Barba | A61K 8/062 |

FOREIGN PATENT DOCUMENTS

| | | |
|---|---|---|
| CN | 1777376 A | 5/2006 |
| CN | 101711727 A | 5/2010 |
| CN | 101854910 A | 10/2010 |
| CN | 101926747 A | 12/2010 |
| EP | 0 951 897 A2 | 10/1999 |
| EP | 1 621 101 A1 | 2/2006 |
| FR | 2 858 555 A1 | 2/2005 |
| FR | 2 923 381 A1 | 5/2009 |
| FR | 2 936 420 A1 | 4/2010 |
| FR | 2 968 520 A1 | 6/2012 |
| JP | S49-97092 U | 8/1974 |
| JP | H11-255619 A | 9/1999 |
| JP | 2002-370963 A | 12/2002 |
| JP | 2004-337598 A | 12/2004 |
| JP | 2011-500979 A | 1/2011 |
| KR | 100852725 B1 | 8/2008 |
| WO | 89/01771 A1 | 3/1989 |
| WO | 01/19333 A1 | 3/2001 |
| WO | 2006/043544 A1 | 4/2006 |
| WO | 2006057071 A1 | 6/2006 |
| WO | 2009/052359 A2 | 4/2009 |
| WO | 2009/052360 A1 | 4/2009 |
| WO | 2013/030485 A2 | 3/2013 |

OTHER PUBLICATIONS

May 2, 2019 Office Action issued in U.S. Appl. No. 15/314,978.
Feb. 19, 2019 Office Action issued in Chinese Application No. 201580028994.0.
Mar. 25, 2019 Office Action issued in Japanese Application No. 2017-515275.
Oct. 7, 2019 Office Action issued in U.S. Appl. No. 15/315,337.
Oct. 18, 2019 Office Action issued in U.S. Appl. No. 15/314,978.
May 28, 2020 Office Action issued in U.S. Appl. No. 15/314,978.
Mar. 19, 2020 Office Action issued in U.S. Appl. No. 15/315,337.
Translation of Nov. 6, 2017 Office Action issued in Japanese Patent Application No. 2017-515276.
Sep. 8, 2015 International Search Report issued in International Patent Application No. PCT/IB2015/054052.
Sep. 8, 2015 International Search Report issued in International Patent Application No. PCT/IB2015/054050.
U.S. Appl. No. 15/314,978, filed Nov. 30, 2016 in the name of Henri Samain et al.
U.S. Appl. No. 15/315,337, filed Nov. 30, 2016 in the name of Henri Samain et al.
Sep. 30, 2020 Office Action issued in U.S. Appl. No. 15/315,337.

\* cited by examiner

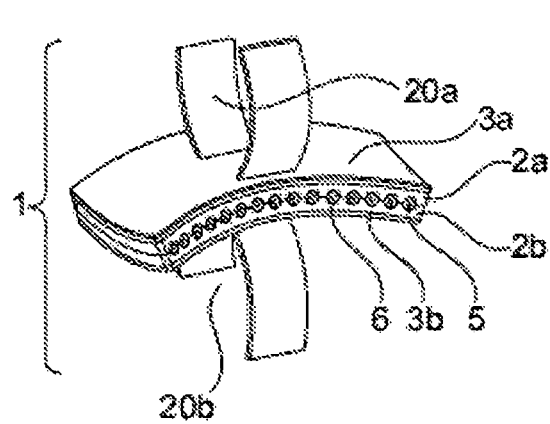
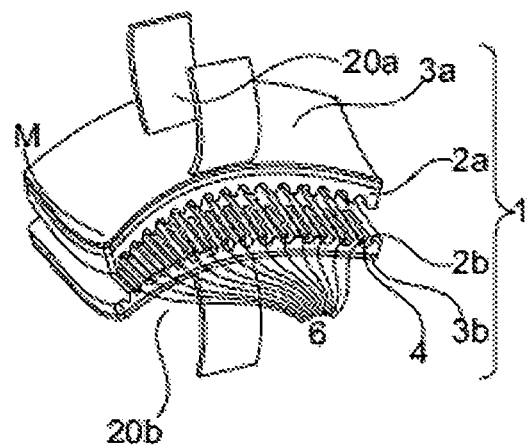
Fig. 4A   Fig. 4B
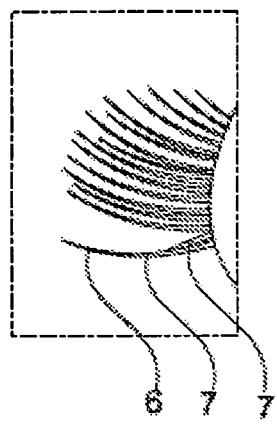
Fig. 5
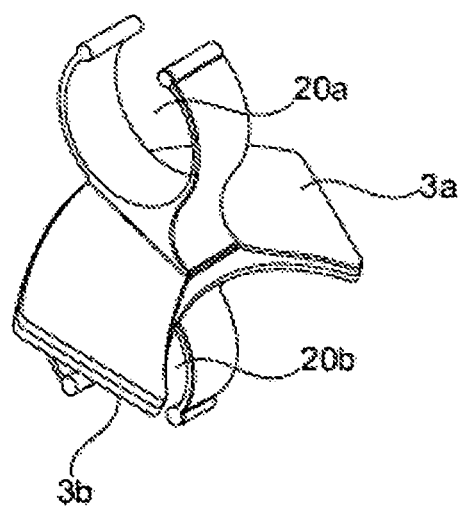
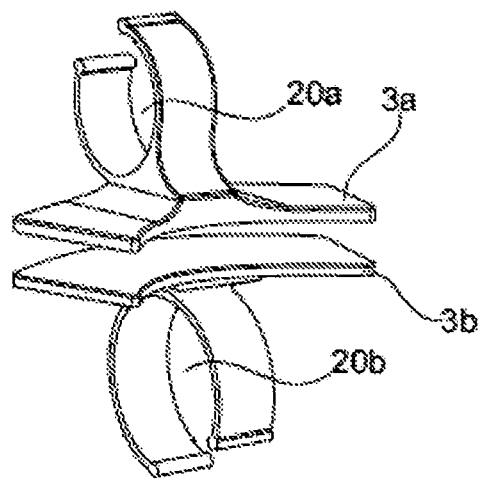
Fig. 6A   Fig. 6B

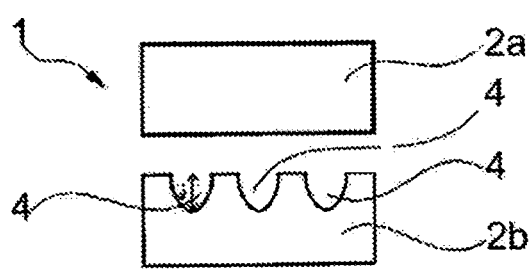
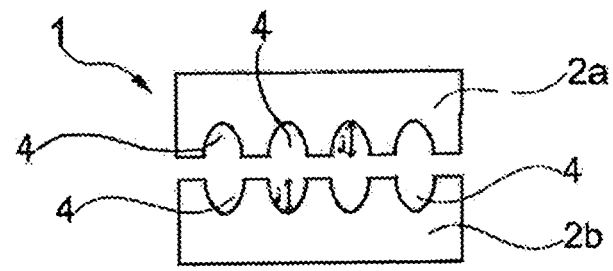
Fig. 7A    Fig. 7B
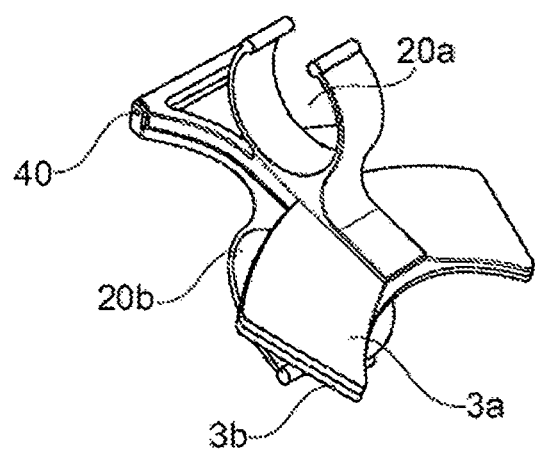
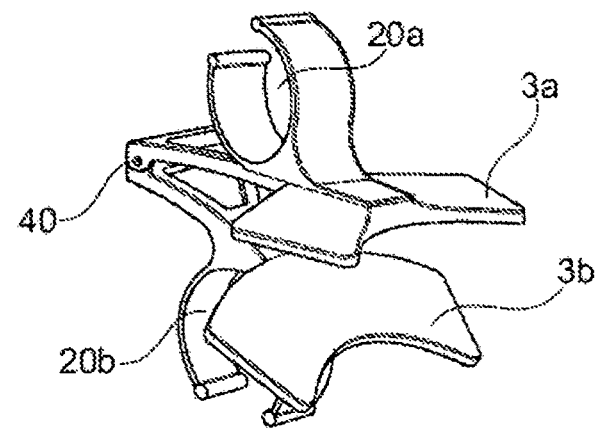
Fig. 8A    Fig. 8B
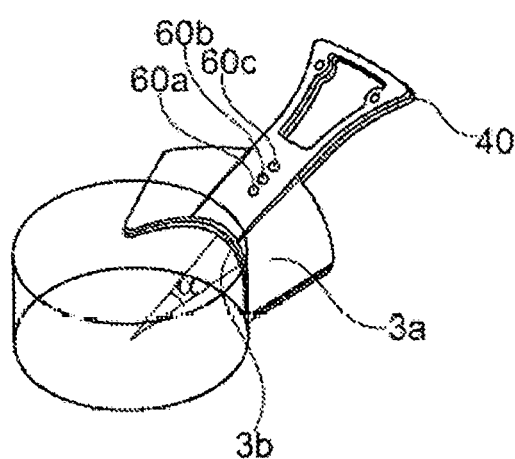
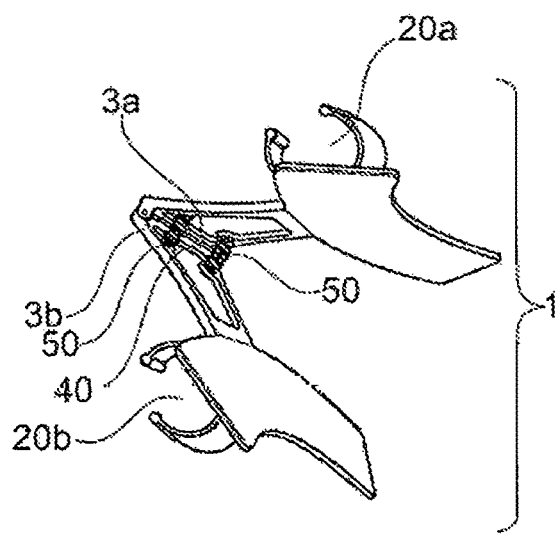
Fig. 9    Fig. 10

Fig. 15A
Fig. 15B
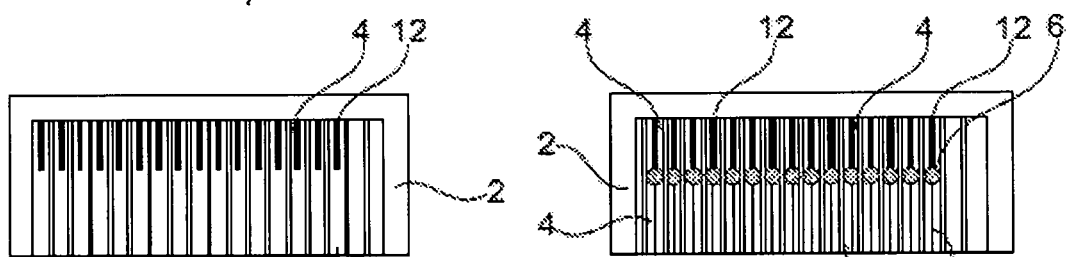
Fig. 16A  Fig. 16B
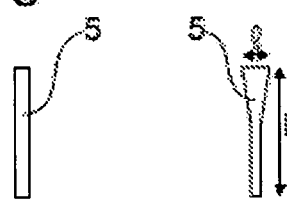 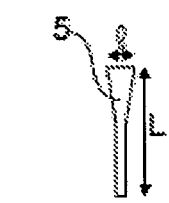 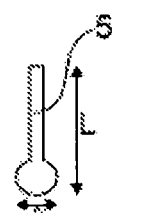 
Fig. 17A  Fig. 17B  Fig. 17C  Fig. 17D
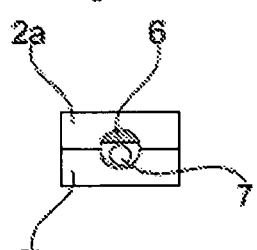 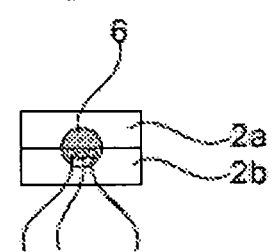 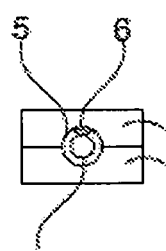 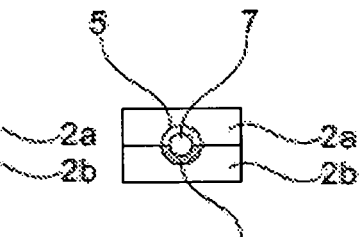
Fig. 18A  Fig. 18B  Fig. 19A  Fig. 19B
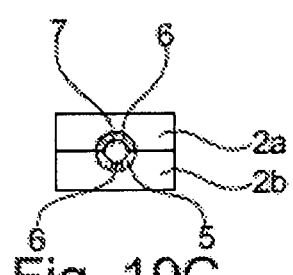 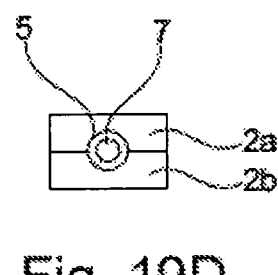 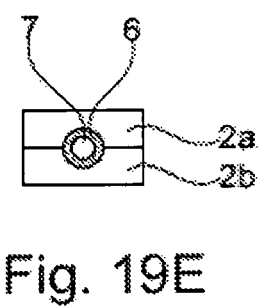
Fig. 19C  Fig. 19D  Fig. 19E

COSMETIC TREATMENT OF KERATIN FIBRES

The present invention aims to provide, for the field of keratin fibre care and/or makeup, a novel treatment which is quite particularly advantageous from the viewpoint of the new technical performance levels that it confers.

The term "keratin fibres" is intended to mean preferably human keratin fibres, in particular the eyelashes, the eyebrows, body hair and the hair, and preferentially the eyelashes or the eyebrows.

Generally, keratin fibres, and more particularly eyelashes, are commonly made up in order to confer thereon greater visibility and/or an original appearance.

In order to achieve this objective, the makeup technique most used is the application of mascara. The latter is generally effective, but it remains, however, to be improved in terms of gain in visibility.

To date, this gain is essentially obtained by increasing the amount of material deposited on the eyelashes via an increased repetition of the number of brushstrokes dedicated to the application of the composition to the surface of the eyelashes. However, this solution is not satisfactory.

Indeed, at each new deposit, material is also removed. In addition, the creation of unattractive overloads and/or agglomerates is generally observed.

Finally, this makeup method does not make it possible to obtain certain aesthetic effects which are highly appreciated by users, for instance the obtaining of a coating on the eyelashes which is very smooth, or even has an advantageous gloss provided by this smoothing effect.

The documents FR 2 936 420 A1, FR 2 923 381 A1, US 2007/286831 A1 and WO 2006/043544 A1 disclose application of mascara with mascara brushes.

Another makeup technique known to increase eyelash visibility is based on the use of additional fibres, for example false eyelashes, which are in particular stuck to the natural eyelashes.

A first variant of this technique consists in sticking false eyelash fringes to the eyelid. Such false eyelash fringes, and also the processes for producing them, are described in U.S. Pat. No. 2,421,432 and U.S. Pat. No. 3,559,657. Nevertheless, putting them on remains difficult and the result remains not very natural. In addition, persistence is weak, and generally limited to a day.

A second variant of this technique consists in sticking false eyelashes one by one to the eyelashes. Although longer lasting, this technique is expensive, takes a long time to perform, and can only be carried out by an individual who works in the profession.

There remains therefore a need for a makeup method which makes it possible to obtain effects of large volume and/or of great length, and which does not have the above-mentioned drawbacks. In particular, there remains a need for a method for making up keratin fibres which makes it possible to easily and rapidly create new effects on the keratin fibres, including the smooth and glossy coating effect, of sheath type.

The invention aims specifically to meet these needs.

Thus, a subject of the present invention is a cosmetic assembly, of use for the treatment of keratin fibres, in particular the eyelashes and the eyebrows, comprising:

a cosmetic composition having a melting point of between 40° C. and 120° C., and comprising at least 15% by weight of meltable compound(s), relative to the total weight of the composition; and a device (1) comprising a mould (2), the mould (2) comprising at least one cavity (5), and preferably several cavities (5), into which or each of which at least one of said fibres can be at least partially introduced for the purposes of moulding said composition onto at least one part of said fibre(s) present in the cavity or cavities (5).

Against all expectations, the invention makes it possible to accurately and reproducibly control the shape of the deposit of composition on the fibres treated, regardless of the dexterity of the individual. Furthermore, this makeup method makes it possible to obtain makeup results thus far unobtainable using conventional techniques. In particular, it makes it possible to significantly extend the length of the keratin fibres and to increase the thickness of the makeup deposit, while providing a smooth and homogeneous, or even glossy, effect. Moreover, it also makes it possible to integrate, into the sheath of makeup produced at the surface of the eyelashes, additional fibres like those considered for false eyelashes.

According to another of its aspects, a subject of the invention is also a process for cosmetic treatment of one or more keratin fibres, in particular of one or more eyelashes or eyebrows, comprising at least the step consisting in moulding a cosmetic composition having a melting point of between 40° C. and 120° C., and comprising at least 15% by weight of meltable compound(s), relative to the total weight of the composition, onto at least one part of said fibres, by means of one or more cavities (5), of a mould (2), into which said fibres are at least partially introduced.

According to yet another of its aspects, the present invention relates to the use of a cosmetic composition having a melting point of between 40° C. and 120° C., and comprising at least 15% by weight of meltable compound(s), relative to the total weight of the composition, for application thereof as a moulding material in at least one cavity of a mould, for the purposes of depositing on keratin fibres, in particular eyelashes and eyebrows, via the application of said mould to said fibres.

Cosmetic Composition

As previously mentioned, a cosmetic composition in an assembly according to the invention has a melting point of between 40° C. and 120° C., and comprises at least 15% by weight of meltable compound(s), relative to the total weight of the composition.

In particular, a cosmetic composition according to the invention has a melting point of between 40° C. and 100° C., preferably between 45° C. and 85° C.

For the purposes of the invention, the melting point corresponds to the temperature of the most endothermic peak observed in thermal analysis (DSC) as described in the standard ISO 11357-3; 1999. The melting point may be measured using a differential scanning calorimeter (DSC), for example the calorimeter sold under the name "DSC Q2000" by the company TA Instruments.

The measuring protocol is as follows:

A 5 mg sample placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature rise ranging from −20° C. to 100° C. at a heating rate of 5° C./minute. During the second temperature rise, the following parameters are measured:

the melting point (Tr) of the sample, which corresponds to the temperature value of the most endothermic peak of the observed melting curve, representing the variation in the difference in power absorbed as a function of the temperature;

Δhf: the fusion enthalpy of the sample, corresponding to the integral of the entire obtained melting curve. Said fusion enthalpy is the amount of energy required to make the composition pass from the solid state to the fluid state. It is expressed in J/g.

Such a cosmetic composition may be fluid or solid at 25° C. and at 1 atm.

It may be aqueous or anhydrous, and preferably anhydrous.

It may have a solids content of greater than or equal to 42% by weight, in particular greater than or equal to 45% by weight, or even greater than or equal to 48% by weight, and preferentially greater than or equal to 50% by weight, relative to the total weight of the composition.

For the purposes of the present invention, the term "solids content" denotes the content of non-volatile matter.

The solids content (abbreviated as SC) of a composition according to the invention is measured using a "Halogen Moisture Analyser HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is in particular described in the documentation of the apparatus supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 120° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content (expressed as weight percentage)=100×(dry mass/wet mass).

According to a first embodiment variant, a cosmetic composition according to the invention is fluid at ambient temperature.

For the purposes of the invention, the description "fluid" is intended to characterize the fact that a composition according to the invention is not solid. In other words, it manifests a fluidity sufficient to have flow properties. A composition of mascara type is, for example, representative of this type of fluidity.

In particular, a composition according to the invention may advantageously have a viscosity of less than 100 Pa·s, preferably between 0.1 Pa·s and 50 Pa·s, and better still between 1 Pa·s and 30 Pa·s, at ambient temperature and pressure, the viscosity being in particular measured using a Rheomat RM100®.

Such a composition may be aqueous or anhydrous.

It may be in the form of oil-in-water emulsions, as is the case for wax-in-water emulsions. It may also be in the form of a dispersion of wax particles in an anhydrous medium, as is the case with a dispersion of wax in isododecane.

According to this first embodiment variant, a cosmetic composition according to the invention may comprise from 15% to 60% by weight, preferably from 18% to 55% by weight and even better still from 20% to 50% by weight of meltable compound(s), relative to the total weight of the composition.

According to a second embodiment variant, a cosmetic composition according to the invention is solid at ambient temperature.

For the purposes of the invention, the description "solid" is intended to characterize the fact that a composition according to the invention is not liquid. In other words, it manifests a rigidity sufficient to not have flow properties.

A composition according to the invention may thus advantageously have a viscosity greater than 1000 Pa·s, preferably greater than 10 000 Pa·s, at ambient temperature and pressure.

Such a composition may be aqueous, in particular in the form of an emulsion of the meltable compound(s) in water, or anhydrous. In particular, it may be in the form of a dispersion of the meltable compound(s) in an organic, preferably volatile, preferentially hydrocarbon-based, solvent.

Such a cosmetic composition is preferably anhydrous.

According to this second embodiment variant, a cosmetic composition according to the invention comprises from 40% to 100% by weight, preferably from 60% to 100% by weight and even better still from 80% to 100% by weight of meltable compound(s), relative to the total weight of the composition.

A composition according to the invention may be subjected to heating means before and/or during application.

These heating means are suitable for melting at least one part of the meltable compound(s) of the cosmetic composition.

The composition may be locally heated to a temperature greater than or equal to 45° C., or even greater than or equal to 50° C., or else greater than or equal to 55° C.

The temperature to which at least part of the composition is heated may be inclusively between 45° C. and 120° C., better still 45° C. and 85° C.

The temperature may be measured, for example, at the surface using an infrared pyrometer, for example a Fluke® brand machine.

Only the heated composition can come into contact with the keratin fibres, for example the eyelashes, during the application.

It is understood that the temperature of the cosmetic composition must not lead to a risk of burning at the time of application.

Thus, when the composition is heated before application, a waiting time between the moment at which the composition is heated and the application to the keratin materials may optionally be necessary.

According to one embodiment variant, the composition is heated simultaneously with its application to the keratin fibres.

According to another embodiment variant, the composition is heated before and during its application to the keratin fibres.

The total heat of fusion of the composition is the heat consumed by the composition between −20° C. and 120° C. The total heat of fusion of the composition is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999.

The measuring protocol is as follows:

A 5 mg sample of composition is placed in a crucible and then subjected to a first temperature rise ranging from −20° C. to 120° C., at a heating rate of 10° C./minute, and is then cooled from 120° C. to −20° C. at a cooling rate of 10° C./minute. The sample is maintained at −20° C. for 5 minutes and finally subjected to a second temperature rise ranging from −20° C. to 100° C. at a heating rate of 5° C./minute.

During the second temperature rise, the variation in the difference in power absorbed by an empty crucible and by the crucible containing the sample of the composition is measured as a function of the temperature. The melting point of the compound is the temperature value corresponding to the top of the peak of the curve representing the variation in the difference in power absorbed as a function of the temperature.

The heat of fusion of the composition consumed at the temperature Tc is the amount of energy Δh required to make the composition pass from the solid or very viscous state at −20° C. to the state of the composition at the temperature Tc. It is expressed in J/g.

According to one embodiment of the invention, the cosmetic composition is chosen such that, when said composition is heated to the temperature Tc, the ratio of the heat consumed between −20° C. and Tc by the composition to the total heat consumed Δh between −20° C. and 120° C. is greater than 0.4.

This relationship is confirmed, for example, for a temperature Tc of the composition of between 45° C. and 85° C.

The choice of the temperature Tc to which the composition is brought by the heating means may thus be made so that said ratio is greater than or equal to 0.4, for example greater than 0.5. In other words, heating is performed to a temperature such that the ratio of the heat supplied to heat the sample of composition to the temperature Tc to the total heat is greater than or equal to 0.4, such a parameter being measured according to the DSC protocol described above.

The composition in accordance with the invention is capable of passing from a solid state to an at least partially liquid or preferably even totally liquid state, and of doing so reversibly.

As mentioned above, a composition according to the invention comprises a content of meltable compound(s) of greater than 15% by weight, relative to the total weight of the composition. Preferably, it may have a content of meltable compound(s) ranging from 15% to 100%, better still from 20% to 95% by weight, relative to the total weight of the composition.

For the purposes of the invention, the meltable compound(s) advantageously has (have) a melting point of between 40° C. and 120° C.

Thus, preferably, a cosmetic assembly, of use for the treatment of keratin fibres, comprises a cosmetic composition having a melting point of between 40° C. and 120° C., and comprises at least 15% by weight of meltable compound(s) having a melting point of between 40° C. and 120° C., relative to the total weight of the composition; and a device comprising a mould, the mould comprising at least one cavity, into which or each of which at least one of said fibres can be at least partially introduced, for the purposes of moulding said composition onto at least one part of said fibre(s) present in the cavity or cavities.

Preferably, this (these) compound(s) can be chosen from thermoplastic polymers, waxes, semi-crystalline polymers, and mixtures thereof.

Thus, according to one particular embodiment, said meltable compound(s) may have crystallizable chains.

In this embodiment, the cosmetic composition is then heated to a temperature Tc such that at least one part of the crystallizable chains of the multiple compound(s) is at least partially, or even totally, melted. The solid/liquid change of state is thus at least partly due to the melting of a crystalline part of the meltable compound(s).

Preferably, the meltable compound(s) according to the invention are not in the form of a particulate dispersion in a solvent medium.

Thermoplastic Polymer

For the purposes of the present invention, the term "thermoplastic polymer" is intended to mean a polymer which softens when hot and which can be moulded while retaining its shape after cooling.

The thermoplastic polymers that can be used in the context of the present invention are any polymer or copolymer or any blend of polymers and/or copolymers having the property of being thermoplastic.

Among the thermoplastic polymers, mention may in particular be made of polyethylene, polystyrene, polyamides, polyvinyl chloride, polyethylene terephthalate, and blends thereof.

Mention may also be made of aliphatic polyesters, and in particular polyhydroxyalkanoates (PHAs), such as poly-3-hydroxybutyrate (PHB), polyhydroxyvalerate (PHV) or polyhydroxyhexanoate (PHH), polylactic acids (PLAs), polybutylene succinates (PBSs), polycaprolactones (PCLs), polyanhydrides, polyvinyl alcohols, and derivatives thereof, acetate esters, such as acetate/polyvinyl (PVAc) copolymer, starch derivatives, polysaccharides, including in particular cellulose derivatives such as cellulose esters, and derivatives thereof, in particular celluloids or cellulose ethers, and mixtures thereof.

In particular, among the cellulose esters, mention may be made of cellulose acetate, cellulose triacetate, cellulose propionate, cellulose acetate propionate, cellulose acetate butyrate, and cellulose sulfate, and mixtures thereof.

Among the cellulose ethers, mention may in particular be made of methylcellulose, ethylcellulose, ethylmethycellulose, hydroxyethylcellulose, hydroxypropylcellulose (HPC), hydroxyethylmethylcellulose, hydroxypropylmethylcellulose (HPMC), ethylhydroxyethylcellulose, carboxymethylcellulose (CMC), and mixtures thereof.

Among the acetate esters, mention may in particular be made of acetate/polyvinyl copolymers, including in particular ethylene-vinyl acetate (EVA) and derivatives thereof. For example, mention may be made of EVA/ethylcellulose or EVA/starch copolymers.

As thermoplastic polymer quite particularly suitable for a composition according to the invention, mention may preferably be made of ethylene-vinyl acetate (EVA), in particular sold under the name Evatane 28-800 by the company Arkema.

In a cosmetic composition according to the invention, use may in particular be made of thermoplastic polymers formulated in a mixture, such as the mixture of ethylene-vinyl acetate and paraffin sold under the name Cool Bind 34-1300® by the company National Starch.

Preferably, the film-forming polymers under consideration in the context of the present invention are distinct from particulate dispersions of latex type.

Wax

The term "wax" is intended to mean in general a lipophilic compound that is solid at ambient temperature (25° C.), with a reversible solid/liquid change in state, having a melting point of greater than or equal to 30° C., which may be up to 200° C. and in particular up to 120° C.

For the purposes of the invention, the melting point corresponds to the temperature of the most endothermic peak observed in thermal analysis (DSC) as described in the standard ISO 11357-3; 1999. The melting point of the wax may be measured using a differential scanning calorimeter (DSC), for example the calorimeter sold under the name "MDSC 2920" by the company TA Instruments.

The measuring protocol is as follows:

A 5 mg sample of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature rise ranging from −20° C. to 100° C. at a heating rate of 5° C./minute. During the second temperature rise, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at ambient temperature of animal, vegetable, mineral or synthetic origin, and mixtures thereof.

The waxes, for the purposes of the invention, may be those used generally in the cosmetic or dermatological fields. They may in particular be polar or apolar, and hydrocarbon-based, silicone and/or fluoro waxes, optionally comprising ester or hydroxyl functions. They may also be of natural or synthetic origin.

a) Apolar Waxes

For the purposes of the present invention, the term "apolar wax" is intended to mean a wax of which the solubility parameter at 25° C. as defined below, $\delta_a$, is equal to 0 $(J/cm^3)^{1/2}$.

The definition and calculation of the solubility parameters in the Hansen three-dimensional solubility space are described in the article by C. M. Hansen: *The three-dimensional solubility parameters*, J. Paint Technol. 39, 105 (1967).

According to this Hansen space:
- $\delta_D$ characterizes the London dispersion forces derived from the formation of dipoles induced during molecular impacts;
- $\delta_p$ characterizes the Debye interaction forces between permanent dipoles and also the Keesom interaction forces between induced dipoles and permanent dipoles;
- $\delta_h$ characterizes the specific interaction forces (such as hydrogen bonding, acid/base, donor/acceptor, etc.); and
- $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

Apolar waxes are in particular hydrocarbon-based waxes constituted solely of carbon and hydrogen atoms, and free of heteroatoms such as N, O, Si and P.

The apolar waxes are chosen from microcrystalline waxes, paraffin waxes, ozokerite and polyethylene waxes, and mixtures thereof.

An ozokerite that may be mentioned is Ozokerite Wax SP 1020 P.

As microcrystalline waxes that may be used, mention may be made of Multiwax W 445® sold by the company Sonneborn, and Microwax HW® and Base Wax 30540® sold by the company Paramelt, and Cerewax° No. 3 sold by the company Baerlocher.

As microwaxes that may be used in the compositions according to the invention as apolar wax, mention may be made in particular of polyethylene microwaxes such as those sold under the names Micropoly 200®, 220®, 220L®, and 250S® by the company Micro Powders.

Polyethylene waxes that may be mentioned include Performalene 500-L Polyethylene and Performalene 400 Polyethylene sold by New Phase Technologies, and Asensa® SC 211 sold by the company Honeywell.

b) Polar Wax

For the purposes of the present invention, the term "polar wax" is intended to mean a wax of which the solubility parameter at 25° C., δa, is other than 0 $(J/cm^3)$".

In particular, the term "polar wax" is intended to mean a wax of which the chemical structure is formed essentially from, or even consists of, carbon and hydrogen atoms, and comprising at least one highly electronegative heteroatom such as an oxygen, nitrogen, silicon or phosphorus atom.

The polar waxes may in particular be hydrocarbon-based, fluoro or silicone waxes.

Preferentially, the polar waxes may be hydrocarbon-based waxes.

The term "hydrocarbon-based wax" is intended to mean a wax formed essentially from, or even constituted of, carbon and hydrogen atoms, and optionally oxygen and nitrogen atoms, and that does not contain any silicon or fluorine atoms. It may contain alcohol, ester, ether, carboxylic acid, amine and/or amide groups.

According to the invention, the term "ester wax" is intended to mean a wax comprising at least one ester function. According to the invention, the term "alcohol wax" is intended to mean a wax comprising at least one alcohol function, i.e. comprising at least one free hydroxyl (OH) group.

In particular, use may be made, as polar waxes, of those chosen from:

i) waxes of formula $R_1COOR_2$ in which R1 and $R_2$ represent linear, branched or cyclic aliphatic chains in which the number of atoms ranges from 10 to 50, which may contain a heteroatom such as O, N or P and whose melting point ranges from 25 to 120° C.;

ii) bis(1,1,1-trimethylolpropane) tetrastearate, sold under the name Hest 2T-4S® by the company Heterene;

iii) diester waxes of a dicarboxylic acid of general formula $R^3$—(—OCO—$R^4$—COO—$R^5$), in which $R^3$ and $R^5$ are identical or different, preferably identical, and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not comprise one or more unsaturations and which is preferably linear and unsaturated;

iv) mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol;

v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax; montan wax, orange wax, laurel wax, hydrogenated jojoba wax, sunflower wax, lemon wax, olive wax or berry wax.

According to another embodiment, the polar wax may be an alcohol wax. According to the invention, the term "alcohol wax" is intended to mean a wax comprising at least one alcohol function, i.e. comprising at least one free hydroxyl (OH) group. Alcohol waxes that may be mentioned include for example the $C_{30-50}$ alcohol wax Performacol® 550 Alcohol from New Phase Technologies, stearyl alcohol and cetyl alcohol.

It is also possible to use silicone waxes, which may advantageously be substituted polysiloxanes, preferably of low melting point.

The term "silicone wax" is intended to mean an oil comprising at least one silicon atom, and in particular comprising Si—O groups.

Among the commercial silicone waxes of this type, mention may be made in particular of those sold under the names Abilwax 9800, 9801 or 9810 (Goldschmidt), KF910 and KF7002 (Shin-Etsu), or 176-1118-3 and 1.76-11481 (General Electric).

The silicone waxes that may be used may also be alkyl or alkoxy dimethicones, and also $(C_{20}$-$C_{60})$alkyl dimethicones, in particular $(C_{30}$-$C_{45})$alkyl dimethicones, such as the silicone wax sold under the name SF-1642 by the company GE-Bayer Silicones or $C_{30-45}$ alkyl dimethylsilyl polypropylsilsesquioxane under the name SW-8005® C30 Resin Wax by the company Dow Corning.

In the context of the present invention, mention may be made, by way of particularly advantageous wax, of beeswax, for example the product sold under the name White Beeswax SP-453P by the company Strahl & Pitsch, or a paraffin wax, Semi-Crystalline Polymer The cosmetic composition according to the invention may comprise at least one semi-crystalline polymer. Preferably, the semi-crystalline polymer has an organic structure, and a melting point of greater than or equal to 30° C.

For the purposes of the invention, the term "semi-crystalline polymer" is intended to mean polymers comprising a crystallizable portion and an amorphous portion and having a first-order reversible change of phase temperature, in particular of melting point (solid-liquid transition). The crystallizable part is either a side chain (or pendent chain) or a block in the backbone.

When the crystallizable part of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable part is a chain that is pendent on the backbone, the semi-crystalline polymer may be a homopolymer or a copolymer.

The melting point of the semi-crystalline polymer is preferably less than 120° C.

The melting point of the semi-crystalline polymer is preferably greater than or equal to 40° C. and less than 85° C.

The semi-crystalline polymer(s) according to the invention are solid at ambient temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. The melting point under consideration is the point corresponding to the temperature of the most endothermic peak in the thermogram.

Besides the crystallizable chains or blocks, the blocks of the polymers are amorphous. For the purposes of the invention, the term "crystallizable chain or block" is intended to mean a chain or block which, if it were alone, would change from the amorphous state to the crystalline state reversibly, depending on whether the temperature is above or below the melting point. For the purposes of the invention, a "chain" is a group of atoms, which are pendent or lateral relative to the polymer backbone, A "block" is a group of atoms belonging to the backbone, this group constituting one of the repeating units of the polymer.

The crystallizable blocks or chains of the semi-crystalline polymers may represent at least 30% and better still at least 40% of the total weight of each polymer. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers containing crystallizable side chains, these side chains are advantageously in random or statistical form.

The semi-crystalline polymers of the invention may be of synthetic origin. In particular, the semi-crystalline polymer may be chosen from:

homopolymers and copolymers comprising units resulting from the polymerization of one or more monomers bearing crystallizable hydrophobic side chain(s), polymers bearing in the backbone at least one crystallizable block, polycondensates of aliphatic or aromatic or aliphatic/aromatic polyester type, copolymers of ethylene and propylene prepared via metallocene catalysis, and acrylate/silicone copolymers.

The semi-crystalline polymers that may be used in the invention may be chosen in particular from:

block copolymers of polyolefins of controlled crystallization, whose monomers are described in EP 0 951 897, polycondensates, in particular of aliphatic or aromatic or aliphatic/aromatic polyester type, copolymers of ethylene and propylene prepared via metallocene catalysis, homopolymers or copolymers bearing at least one crystallizable side chain and homopolymers or copolymers bearing in the backbone at least one crystallizable block, such as those described in document U.S. Pat. No. 5,156,911, such as the $(C_{10}$-$C_{30})$alkyl polyacrylates corresponding to the Intelimer® products from the company Landec described in the brochure Intelimer®

*Polymers*, Landec IP22 (Rev. 4-97), for example the product Intelimer® IPA 13-1. from the company Landec, which is a polystearyl acrylate with a molecular weight of about 145 000 and a melting point of 49° C., homopolymers or copolymers bearing at least one crystallizable side chain, in particular containing fluoro group(s), as described in document WO 01/19333, acrylate/silicone copolymers, such as copolymers of acrylic acid and of stearyl acrylate bearing polydimethylsiloxane grafts, copolymers of stearyl methacrylate bearing polydimethylsiloxane grafts, copolymers of acrylic acid and of stearyl methacrylate bearing polydimethylsiloxane grafts, copolymers of methyl methacrylate, butyl methacrylate, 2-ethylhexyl acrylate and stearyl methacrylate bearing polydimethylsiloxane grafts. Mention may be made in particular of the copolymers sold by the company Shin-Etsu under the names KP-561 (CTFA name: acrylates/dimethicone), KP-541 (CTFA name: acrylates/dimethicone and isopropyl alcohol), KP-545 (CTFA name: acrylates/dimethicone and cyclopentasiloxane), and mixtures thereof.

In the context of the present invention, as particularly advantageous semi-crystalline polymers, mention may be made of poly($C_{10}$-$C_{30}$)alkyl acrylates, for example the product sold under the name Intelimer IPA 13-1 NG by the company Air products and Chemical.

Preferably, in the context of the present invention, the meltable compound(s) is (are) chosen from ethylene-vinyl acetate (EVA), a beeswax, a paraffin wax, a poly($C_{10}$-$C_{30}$) alkyl acrylate, a vinyl acetate/allyl stearate copolymer, and mixtures thereof.

In the context of the present invention, mention may in particular be made of vinyl acetate/allyl stearate copolymers, for example the product sold under the name Mexomere PQ by the company Chimex.

Aqueous Phase

The cosmetic composition of an assembly according to the invention may comprise an aqueous phase, which may form a continuous phase of the composition.

The aqueous phase may comprise water. It may also comprise at least one water-soluble solvent.

In the context of the present invention, the term "water-soluble solvent" denotes a compound that is liquid at ambient temperature and water-miscible.

The water-soluble solvents that may be used in the compositions according to the invention may also be volatile.

Among the water-soluble solvents that may be used in the compositions in accordance with the invention, mention may be made in particular of lower monoalcohols containing from 1 to 5 carbon atoms such as ethanol and isopropanol, and glycols containing from 2 to 8 carbon atoms such as ethylene glycol, propylene glycol, 1,3-butylene glycol and dipropylene glycol.

The aqueous phase, for example composed of water and optionally a water-miscible solvent, is generally present in a composition according to the invention in a content ranging from 30% to 80% by weight, preferably ranging from 40% to 70% by weight, relative to the total weight of the composition.

Volatile Solvent

A cosmetic composition according to the present invention may comprise one or more volatile solvent(s).

In the context of the present invention, the term "volatile solvent" is intended to mean a compound which is liquid at ambient temperature (20° C.) and atmospheric pressure, having a vapour pressure at 20° C. of greater than 0.1 mmHg and preferably of between 0.1.and 300 mmHg, even more preferentially between 0.5 and 200 mmHg.

This volatile solvent may be water, a non-silicone organic solvent, a silicone organic solvent, or mixtures thereof. By way of volatile non-silicone organic solvent, mention may be made of:

$C_1$-$C_4$ volatile alkanols, such as ethanol or isopropanol;

$C_5$-$C_7$ volatile alkanes, such as n-pentane, hexane, cyclopentane, 2,3-dimethylbutane, 2,2-dimethylbutane, 2-methylpentane or 3-methylpentane;

esters of liquid $C_1$-$C_{20}$ acids and of volatile $C_1$-$C_8$ alcohols, such as methyl acetate, n-butyl acetate, ethyl acetate, propyl acetate, isopentyl acetate or ethyl 3-ethoxypopionate;

ketones that are liquid at ambient temperature and volatile, such as methyl ethyl ketone, methyl isobutyl ketone, diisobutyl ketone, isophorone, cyclohexanone or acetone;

volatile polyols, such as propylene glycol;

volatile ethers, such as dimethoxymethane, diethoxyethane or diethyl ether;

volatile glycol ethers, such as 2-butoxyethanol, butyl diglycol, diethylene glycol monomethyl ether, propylene glycol n-butyl ether or propylene glycol monomethyl ether acetate;

volatile hydrocarbon-based oils, such as volatile hydrocarbon-based oils having from 8 to 16 carbon atoms, and mixtures thereof, and in particular branched $C_8$-$C_{18}$ alkanes such as $C_8$-$C_{18}$ isoalkanes (also known as isoparaffins), isododecane or isodecane, and, for example, the oils sold under the trade names Isopar or Permethyl, and mixtures thereof. Mention may also be made of isohexyl or isodecyl neopentanoates;

volatile $C_4$-$C_{10}$ perfluoroalkanes, such as dodecafluoropentane, tetradecafluorohexane or decafluoropentane;

volatile perfluorocycloalkyls, such as perfluoromethylcyclopentane, 1,3-perfluorodimethylcyclohexane and perfluorodecaline, sold respectively under the names Flutec PC10, Flutec PC30 and Flutec PC60 by the company F2 Chemicals, and also perfluorodimethylcyclobutane and perfluoromorpholine;

the volatile fluoroalkyl or heterofluoroalkyl compounds corresponding to the following formula:

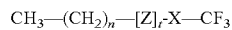

$$CH_3-(CH_2)_n-[Z]_t-X-CF_3$$

in which t is 0 or 1; n is 0, 1, 2 or 3; X is a linear or branched divalent perfluoroalkyl radical containing from 2 to 5 carbon atoms, and Z represents O, S or NR, R being a hydrogen, a —$(CH_2)_n$—$CH_3$ or —$(CF_2)_m$—$CF_3$ radical, m being equal to 2, 3, 4 or 5.

Among the volatile fluoroalkyl or heterofluoroalkyl compounds, mention may in particular be made of the methoxynonafluorobutane sold under the name MSX 4518 (R) and HFE-7100(R) by the company 3M and the ethoxynonafluorobutane sold under the name HFE-7200(R) by the company 3M.

Preferably, the solvent is chosen in such a way that its boiling point is below 200° C.

According to one particular embodiment, the non-silicone organic solvent is chosen from ethanol, isopropanol, acetone and isododecane.

By way of volatile silicone solvent, mention may be made of silicone compounds with a low viscosity, chosen from linear or cyclic silicones having from 2 to 7 silicon atoms, these silicones optionally comprising alkyl or alkoxy groups having from 1 to 10 carbon atoms, for example octamethylcycl otetrasiloxane, decamethylcyclopentasiloxane, dodecamethylcyclohexasiloxane, heptamethylhexyltrisiloxane, heptamethylethyltrisiloxane, heptamethyloctyltrisiloxane, octamethyltrisiloxane, decamethyltetrasiloxane, and mixtures thereof. According to one particular embodiment, the silicone compound is chosen from cyclopentadimethylsiloxane and dodecamethylcyclohexasiloxane.

According to one particular embodiment, the volatile silicone solvent has a viscosity of less than 50 centistokes.

The volatile silicone is preferably cyclic and chosen from decamethylcyclopentasiloxane, octamethyltrisiloxane and decamethyltetrasiloxane.

By way of example, mention may be made of the decamethylcyclopentasiloxane sold under the name DC-245 by the company Dow Corning, the octamethyltrisiloxane sold under the name DC-200 Fluid 1 cst by the company Dow Corning, and the decamethyltetrasiloxane sold under the name DC-200 Fluid 1,5 cst by the company Dow Corning.

This cyclic volatile silicone generally has a low viscosity, for example a viscosity of less than 5 cSt at 25° C.

Preferably, the volatile silicone is cyclic and is the decamethylcyclopentasiloxane sold under the name DC-245 by the company Dow Corning.

Preferably, the cosmetic composition comprises less than 20% of volatile solvent(s), preferably less than 10% of volatile solvent(s), and even more preferentially the cosmetic composition is free of volatile solvent(s).

Colorant

The compositions in accordance with the invention preferably comprise at least one colorant.

This (or these) colorant(s) is (are) preferably chosen from pulverulent substances, liposoluble dyes and water-soluble dyes, and mixtures thereof.

Preferably, the compositions according to the invention comprise at least one pulverulent colorant. The pulverulent colorants may be chosen from pigments and nacres, and preferably chosen from pigments.

The pigments may be white or coloured, inorganic and/or organic, and coated or uncoated. Among the inorganic pigments, mention may be made of metal oxides, in particular titanium dioxide, optionally surface-treated, zirconium, zinc or cerium oxide, and also iron, titanium or chromium oxide, manganese violet, ultramarine blue, chromium hydrate and ferric blue. Among the organic pigments that may be mentioned are carbon black, pigments of D&C type and lakes based on cochineal carmine or on barium, strontium, calcium or aluminium.

The nacres may be chosen from white nacreous pigments such as mica coated with titanium or with bismuth oxychloride, coloured nacreous pigments such as titanium mica with iron oxides, titanium mica with in particular ferric blue or chromium oxide, titanium mica with an organic pigment of the abovementioned type, and also nacreous pigments based on bismuth oxychloride. Examples of nacres that may also be mentioned include natural mica coated with titanium oxide, with iron oxide, with natural pigment or with bismuth oxychloride.

Among the commercially available nacres that may be mentioned are the nacres Timica, Flamenco and Duochrome (on mica base) sold by the company Engelhard, the Timiron nacres sold by the company Merck, the Prestige nacres on mica base sold by the company Eckart and the Sunshine nacres on synthetic mica base sold by the company Sun Chemical.

The nacres may more particularly have a yellow, pink, red, bronze, orange, brown, gold and/or coppery colour or tint.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto.

Preferably, the pigments contained in the compositions according to the invention are chosen from metal oxides.

A composition according to the invention may also comprise at least one particulate or non-particulate, water-soluble or water-insoluble colorant, preferably in a proportion of at least 0.01% by weight relative to the total weight of the composition.

For obvious reasons, this amount is liable to vary significantly with regard to the intensity of the desired colour effect and of the colour intensity afforded by the colorants under consideration, and its adjustment clearly falls within the competence of those skilled in the art.

These colorants may be present in a content ranging from 0.01% to 30% by weight, in particular from 6% to 22% by weight, relative to the total weight of the composition.

Preferably, the colorant(s) is (are) chosen from one or more metal oxides that are present in a content of greater than or equal to 2% by weight relative to the total weight of the composition, and advantageously inclusively between 6% and 22% by weight, relative to the total weight of the composition.

Device

As previously mentioned, a cosmetic assembly according to the invention contains, in addition to a cosmetic composition, a device comprising a mould, the mould comprising at least one cavity, and preferably several cavities, into which or each of which at least one of said fibres can be at least partially introduced, for the purposes of moulding the composition onto at least one part of said fibre(s) present in the cavity or cavities.

Mould

The moulding is carried out in situ in the mould cavity or cavities, and allows the composition to be shaped. Thus, the composition can fit the shape of the mould cavity or cavities.

The mould may comprise one or more imprints, which each at least partially define a mould cavity. Preferably, the mould is not limited to a single cavity. In particular, the mould comprises at least two cavities, preferably at least six cavities, and even more preferentially at least ten cavities.

The mould may comprise at least two parts which each comprise one or more imprints, the imprint(s) of one of the parts being placed opposite the imprint(s) of at least one other part, so as to form the mould cavity or cavities when the parts of the mould are brought together, each of the imprints being in particular of rounded cross section, notably of circular arc, elliptical arc or parabolic cross section, in particular of semicircular cross section.

The mould may comprise at least two parts, one part comprising one or more imprints, each of the imprints being in particular of rounded cross section, notably of circular arc, elliptical arc or parabolic cross section, in particular of semicircular cross section, the other part being devoid of imprint, so as to form the mould cavity or cavities when the parts of the mould are brought together. Such a mould has the advantage of not requiring a great deal of precision when placing the two parts of the mould opposite one another so as to form the cavities.

The imprint(s) may be of rounded cross section to fit the keratin fibre(s) shape.

The imprints may be parallel to one another.

The imprints may be arranged along only one part of the mould, in particular in the front of said mould, i.e. on the side where the keratin fibres are introduced.

Each imprint may have a depth of between 75 gm and 1.5 mm.

The mould may remain motionless relative to the keratin fibres during the moulding of the fibres in its cavity or cavities.

The mould preferably does not move along the keratin fibres during the moulding of the fibres in its cavity or cavities.

The mould may or may not be disposable.

The surface of the mould may be smooth so as to confer on the composition once moulded a smooth external surface and a glossy appearance.

There can not be any relative speed between the keratin fibres and the cavities during the moulding, for example for a period required for the hardening or the drying of the composition, for example a period of typically 10 to 60 seconds.

Mould Cavity

The volume of the cavity or cavities may exceed by at least a factor of 2, better still a factor of 10 to 100, the volume of the part of the keratin fibres filling it or them.

The volume of each cavity may range between 0.08 and 220 mm$^3$.

The cavity or cavities may each have a circular, semicircular, oval or polygonal cross section, which may or may not be constant when moving along the cavity.

The cavity or cavities may each be approximately cylindrical in shape.

The cavity or cavities may each have a decreasing cross section so as to give the fibre(s), once moulded by the composition, a tapered appearance and to facilitate, where appropriate, the demoulding of the fibres by pulling them away.

The cavity or cavities may each have an approximately cylindrical shape on one part of their length and an enlarged, in particular spherical, shape on another part of their length, in particular with a view to moulding a head, for example in the shape of a portion of a sphere, on at least one part of the keratin fibre(s).

The cavity or cavities may each have a length of between 5 and 30 mm and a width, in particular a diameter, of between 150 μm and 3 mm. In the case of a length of 30 mm and a diameter of 3 mm, the volume may be increased by a factor of 50.

Each cavity may have an elongated shape with a curvilinear longitudinal axis which approximately reproduces or which increases the curvature of the keratin fibre(s) introduced, in particular the eyelashes. Thus, the moulding enables to increase keratin fibres visibility while underlining their curvature.

The radius of curvature of the cavity or cavities may be higher than 15 mm. In particular, it can range between 15 and 25 mm.

Each cavity may, on the contrary, have an elongated shape which does not reproduce the curvature of the keratin fibre(s) introduced, having in particular a rectilinear or broken-line longitudinal axis. The cavity or cavities may extend in all directions, in particular transversely to the eyelashes. The cavity or cavities may form patterns of any types, such as waves or grids.

Each cavity may have an elongated shape, with a curvilinear or rectilinear longitudinal axis, and the cavities may have non-parallel respective longitudinal axes.

When the cavity or cavities have an elongated shape, the keratin fibres are preferably introduced into the cavity or cavities along their longitudinal axes.

Although cavities of elongated shape make it possible to perform a more conventional cosmetic treatment of keratin fibres, new effects can be obtained with cavities of non-elongated shape. For example, the cavity or cavities may each have an approximately spherical or polyhedral shape, in particular spherical shape, having a diameter of between 0.4 mm and 5 mm, so as to form balls at the end of the keratin fibres, for example.

Each cavity is preferably closed laterally, so that the composition does not escape laterally during the moulding.

Each cavity may have an elongated shape and be closed at least one of its longitudinal ends.

Each cavity may constitute a space which is substantially entirely closed, notably entirely closed, in the absence of keratin fibre. In this case, one part of each keratin fibre at least partially introduced into a cavity may be gripped between the two parts of the mould that are brought together, while another part of the keratin fibre extends into the cavity. The cavity may be closed on the side where the keratin fibre(s) is (are) introduced, via a flexible wall, which can deform, preferably elastically, so as to allow the keratin fibre(s) to pass into the cavity.

As a variant, each cavity may constitute a semi-open space, in the absence of keratin fibre. In particular, each cavity can delimit a space which is closed with the exception of one end via which the keratin fibre(s) which is (are) at least partially introduced into the cavity communicate(s) with the exterior. Thus, each cavity may open to the exterior, on the side where the keratin fibre(s) is (are) introduced, via an opening through which the keratin fibre(s) is (are) introduced.

The free end of the keratin fibre(s) introduced into the cavity or cavities preferably do not exceed the cavity or cavities.

At least two of the cavities may be not connected. All of the cavities may be not connected.

The cavities may or may not be parallel to one another.

The cavities may be placed at regular intervals, for example according to a step of 1 to 2 mm, centre to centre.

The number of cavities may be greater than or equal to one, in particular greater than or equal to two, preferably greater than or equal to six and more preferably greater than or equal to ten.

Jaws

The cavity or cavities may be formed by bringing two jaws together, in particular according to a translational and/or rotational movement of one of the jaws with respect to the other.

The two jaws can be moved apart at the moment the keratin fibres are introduced and closed again so as to form the cavities into which the keratin fibres are introduced.

The jaws may carry or integrate the mould.

The jaws may be curved, in particular about a geometric axis perpendicular to the longitudinal axis of the mould cavities.

A system where one or both of the jaws slide(s) on columns can be used to move the two jaws apart at the moment the keratin fibres are introduced and to close them again so as to form the cavities.

Use may also be made of a system where the jaws are connected by a hinge.

Use may also be made of a system where the jaws are not connected, and are optionally associated with one another by a guide system.

The two jaws preferably fit together sufficiently well for the composition present in the cavities not to escape.

The jaws may comprise an elastomer material, for example in order to absorb a deformation of the mould.

Mould Deformation

It may be advantageous to deform the mould with the keratin fibres in place in order to reduce the volume of the cavities, and for example to force the composition to be distributed around the fibres introduced into the cavities.

The mould may comprise a flexible, in particular elastomeric, material.

An extensible, in particular elastomeric, mould makes it possible to compress the composition in order to avoid problems of dead volume and/or to force better integration of the fibres into the composition. The mould may be entirely made of flexible, in particular elastomeric, material.

The mould may comprise flexible parts and non-flexible parts. The mould may in particular be surface-covered with flexible, in particular elastomeric, material, for example over a thickness ranging from 0.5 to 2 mm.

The deformation of the mould may be carried out by compression, for example mechanical compression with fingers, or be pneumatic or hydraulic, or by suction. For example, by pulling a trigger, an overpressure can be created between one jaw and the mould, which has the effect of compressing the two parts of the mould onto one another and preventing dead zones.

Demoulding

The composition can be demoulded, extracted from the mould, preferably without losing its cohesion around the keratin fibres and while retaining the surface finish conferred by the mould.

Demoulding of the composition without deterioration is desired.

The mould may be extensible, in particular elastomeric, in order to facilitate demoulding.

The mould cavity or cavities may have a non-stick coating or may have undergone a treatment aimed at conferring non-stick properties. Thus, the mould may comprise at the surface a low-adhesion material, in particular of silicone or PTFE type. A layer of a non-stick product, in particular an oil, a silicone, a PTFE powder or boron nitride, may also be applied to the mould cavity.

The device may comprise an automatic or non-automatic demoulding system in order to act on the mould and/or the composition contained in the cavity or cavities in order to facilitate the separation of the composition-coated fibres from the mould. This demoulding system may comprise a set of small blades or other reliefs which deform the mould by being compressed against said mould. The deformation of the mould can take place at the level of the cavities, thereby facilitating the ejection of the moulded material.

Bridges of composition may connect several cavities to one another after moulding, in an unwanted manner. The device may comprise blades or other reliefs which are used to cut bridges of composition between at least two cavities after moulding. These blades or other reliefs may act by fitting over the bridges between the cavities. These blades may be added to the mould.

The blades or other reliefs which are used to cut the bridges of composition may be carried by one of the jaws. In this case, the other jaw may have a planar surface from the viewpoint of the blade or other relief or a groove into which the blade or other relief fits. The blades or other reliefs may further be placed on the two jaws, in such a way that one blade or other relief of one of the jaws fits over one blade or other relief of the other jaw.

The demoulding of the moulded composition is preferably carried out mechanically, in particular by deformation of the mould, by moving the two jaws away from one another and/or by pulling the keratin fibres out of the mould.

The demoulding of the composition may be carried out, where appropriate, by pulling at one end of one part of the mould in order to separate it from the other part, in the way in which two sheets adhering to one another are separated by peeling. The demoulding of the moulded composition may further, according to one variant, be at least partly carried out physicochemically, in particular by at least partially dissolving, with a solvent, the mould or a film-coating present inside the mould, between said mould and the composition moulded onto the keratin fibres.

Provision of the Composition

At least one part of the composition, in particular the entire composition, may be deposited on at least one of said fibres, better still on each of said fibres, before they are introduced into the mould. In this case, the closing of the mould can distribute the composition in the cavities and, where appropriate, drive the excess composition out of the mould.

At least one part of the cosmetic composition, in particular the entire cosmetic composition, may be initially present in the mould before introduction of the fibre(s) into the mould. This can facilitate the metering of the composition introduced into the mould cavity or cavities. The composition may be contained with the mould in sealed packaging.

At least one part of the composition, in particular the entire composition, may be injected into the mould, via at least one injection channel.

The mould may comprise imprints in which at least one part of the composition, in particular the entire composition, is present before introduction of the keratin fibre(s) into the mould. The imprints define the mould cavities when said mould is closed.

The mould may comprise at least two parts each comprising imprints, at least one part of the composition, in particular the entire composition, being present in at least one part, in particular in all the parts, of the mould, before introduction of the keratin fibre(s) into the mould. The composition for example entirely fills the imprints and is present only in the imprints, before closing of the mould.

The mould may also be prefilled with an excess of the composition so that the material stands higher than the cavity, for example by being slightly curved. In this way, any absence of product around the eyelash is avoided and the formation of a perfect cast is ensured.

Automatism

The device may be automated. A single triggering may make it possible to perform a series of operations, for example filling the cavities with the moulding composition, and an action exerted on the mould so as to deform it in order to perform the demoulding. The closing of the mould may also be automatic.

Device

The device may comprise at least one heating element which serves to increase the temperature of the composition, the increase in the temperature inducing a change of state of the composition, in particular a change from the solid state to the liquid state by melting.

During the temperature increase, the composition may be present in the mould or outside the mould. The composition may be present outside the mould during the increase in its temperature and may be injected in the liquid state into the mould, in particular via at least one injection channel.

The heating may be automatically triggered upon closure of the mould. As a variant, the heating may be triggered before closure of the mould and a visual and/or sound indicator may signal to the user that the desired temperature for closing the mould and/or putting the fibres in place has been reached.

The device may comprise at least one system for admitting material, which serves to introduce a part or all of the cosmetic composition into the mould cavity or cavities, and in particular comprises one or more injection channels communicating with one or more mould cavities. The composition is, for example, contained in a reservoir, and a piston or a pump makes it possible to force it to flow into the mould cavity or cavities.

The device may comprise a heating element which is at least one light element, in particular IR, UV or visible light element, or microwave element, which serves to increase the temperature of the composition, in particular by absorption of the light or microwave radiation by the cosmetic composition.

The jaws may be closed manually.

The device may be in the form of a clamp comprising at least one housing into which at least one of the fingers of one hand, for example the thumb or the index finger, can be introduced so as to move the two jaws apart, in order to make it possible to introduce the keratin fibres and to close them on said fibres.

The device may be in the form of a clamp comprising two housings into which two of the fingers of one hand, for example the thumb and the index finger, can be introduced so as to move the two jaws apart, in order to make it possible to introduce the keratin fibres and to close them on said fibres. Each of these housings may be removable or non-removable. It may or may not be possible for each of these housings to be oriented rotationally.

Cosmetic Treatment Process

As previously mentioned, according to another of its aspects, the present invention also relates to a process for cosmetic treatment of one or more keratin fibres, in particular of one or more eyelashes or eyebrows, comprising at least the step consisting in moulding a cosmetic composition having a melting point of between 40° C. and 120° C., and comprising at least 15% by weight of meltable compound(s), relative to the total weight of the composition, onto at least one part of said fibres, by means of one or more cavities (5), of a mould (2), into which said fibres are at least partially introduced.

In particular, said fibres are, optionally individually, at least partially introduced into said cavities.

The composition may be deposited on at least three quarters of the length of at least one of said fibres, better still on at least three quarters of the length of each of said fibres.

The length of a fibre is measured from the surface of the skin up to its free end when the fibre is placed flat.

The composition may be deposited on just one part of the length of at least one of said fibres, better still on just one part of the length of each of said fibres.

Preferably, the cosmetic composition is brought to a temperature greater than or equal to its melting point.

The cavity or cavities of the mould can be formed by bringing two jaws together, the jaws remaining closed until the composition has solidified.

According to one particular embodiment, the cosmetic composition is moulded onto at least one part of at least one of said keratin fibres and of at least one additional fibre, the cosmetic composition ensuring the attachment of the additional fibre(s) to the keratin fibre(s), in particular with the additional fibre(s) dedicated to extending the keratin fibre(s), with or without axial overlap between the two types of fibres.

Keratin Fibres

The keratin fibres to which the treatment according to the invention applies are preferably human, in particular eyelashes or eyebrows, more preferably eyelashes.

The keratin fibres may be hair. It is thus possible to treat the hair, in particular on a part of the length thereof, for instance the roots, in order to increase the rigidity thereof, and/or the ends in order to improve the appearance thereof.

It is possible to post-treat the keratin fibres, moulded according to the invention, with other products, for example mascara, or by contact with a hot surface.

Each of said fibres may be at least partially introduced into a respective cavity. At least two of said fibres may be at least partially introduced into the same cavity. At least one cavity may contain just one fibre.

Additional Fibres

The assembly and the process according to the invention also make it possible to attach additional fibres to existing keratin fibres via the composition while limiting the visibility of the connection, thereby making it possible to give the keratin fibres a longer and/or thicker appearance.

Thus, the composition may be moulded onto at least one part of at least one of said keratin fibres and of at least one additional fibre. Thus, the device may comprise one or more additional fibres ensuring the attachment of the additional fibre(s) to the keratin fibre(s), in particular with the additional fibre(s) dedicated to extending the keratin fibre(s), with or without axial overlap between the two types of fibres.

The composition may be deposited on just one part of the length of at least one of the keratin fibres and on just one part of the length of at least one additional fibre, better still on just one part of the length of each of the keratin fibres and on just one part of the length of each of the additional fibres.

The additional fibres may be covered with the composition only at their ends directed towards the keratin fibres, preferably over a length of less than 10 mm, and preferably less than 5 mm.

The device may comprise one or more of said additional fibres, prepositioned in the mould cavity or cavities or interlinked with a support which makes it possible to preposition them. This support may be removable or resorbable, for example by washing with water.

The additional fibres may be synthetic fibres of the same colour as the keratin fibres of the user, and in particular may be darker in colour than the eyelashes of the user and in particular black. Typically, the fibres are 50 μm to 200 μm in diameter, and between 5 mm and 25 mm in length, and can be tapered in order to resemble natural eyelashes.

At least one part of the composition, in particular the entire composition, may be deposited on the additional fibre(s) before they are introduced into the mould.

At least one part of the composition, in particular the entire composition, may be deposited on the additional fibre(s) while said fibres are present in the mould.

At least one part of the composition, in particular the entire composition, may be initially present in the mould before introduction of the additional fibres into the mould.

At least one part of the composition, in particular the entire composition, may be injected into the mould, via at least one injection channel.

Heat then makes it possible to attach the additional fibres to the keratin fibres.

The device may comprise two jaws, at least one of the jaws comprising a heating element.

The device may comprise a light source and two jaws, at least one of the two jaws being transparent to at least a part of the radiation emitted by the light source, such that said radiation reaches the composition.

The keratin fibres may be cut prior to their introduction into the mould, in particular in order to give them a length which will make them fit to the arrangement of the additional fibres in the mould.

Other features, advantages and methods of application of the particles and of the preparation process according to the invention will emerge more clearly from the exemplary embodiments of the invention and from the examination of the appended figures, presented by way of non-limiting illustration of the field of the invention and in which:

FIGS. 4A and 4B represent another example of an assembly according to the invention, in the form of a clamp, respectively with the jaws of the mould closed in moulding configuration and open;

FIG. 5 illustrates the deposit of composition obtained on eyelashes after cosmetic treatment;

FIGS. 6A and 6B, 8A and 8B, 10 and 11 represent other examples of devices according to the invention in the form of a clamp, the moulds not being represented, FIGS. 6A and 6B illustrating the same example of a device respectively with the jaws of the mould closed and open, FIGS. 8A and 8B illustrating the same example of a device respectively with the jaws of the mould closed and open;

FIGS. 7A and 7B represent two examples of a mould before closing;

FIG. 9 represents the device from FIG. 8A, the housings having been dismantled;

FIGS. 15A and 15B represent two examples of connection of an additional fibre to an eyelash using a composition according to the invention;

FIGS. 16A and 16B illustrate an example of attachment of additional fibres to eyelashes;

FIGS. 17A to 17D represent, in section, examples of mould cavity shape;

FIGS. 18A and 18B represent respectively a cavity comprising an eyelash and a cavity comprising several eyelashes;

FIGS. 19A to 19E represent, in section, examples of arrangements of the composition according to the invention before moulding, within a mould cavity into which an eyelash is introduced;

FIGS. 1A and 1B represent an example of an assembly according to the invention comprising a device (1) and a cosmetic composition (6) for cosmetic treatment of eyelashes.

Figure 1A:
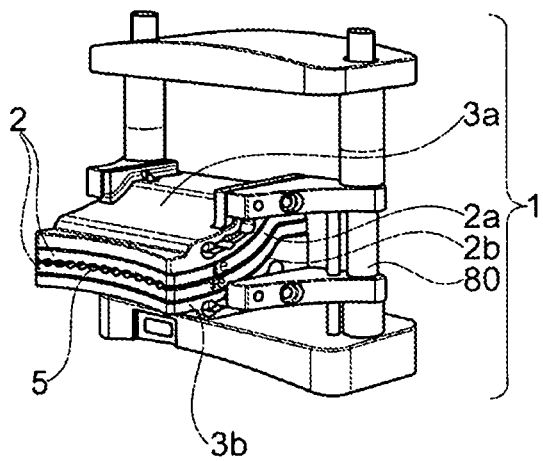
FIGS. 1A and 1B represent an example of an assembly according to the invention, respectively with the jaws of the mould closed in moulding configuration and open.

The device (1) comprises a mould (2) which has two parts (2a) and (2b). The mould (2) preferably comprises an elastomeric material. The two parts (2a) and (2b) of the mould (2) each have a thickness e of approximately 2 mm for example.

The two parts (2a) and (2b) of the mould (2) comprise imprints (4), in the form of grooves of elongated shape. Each part (2a, 2b) comprises, for example, as illustrated, 17 imprints (4), for example of width 1 of approximately 0.5 mm, of length L of approximately 2.5 cm and of approximately semicircular cross section. The imprints (4) of each part (2a, 2b) of the mould (2) are preferably substantially parallel to one another. The imprints are also, preferably as illustrated, evenly spaced out, according to a step p of 1.5 mm, centre to centre.

The device (1) comprises two jaws (3a) and (3b) which carry respectively the mould parts (2a) and (2b).

The two parts of the mould (2) and the jaws (3a) and (3b) may have additional reliefs, so as to be able to accurately place the two parts (2a, 2b) of the mould (2) on each jaw (3a, 3b).

The lower jaw (3b) comprises, in the example under consideration, a temperature-controlled heating element (30).

The lower jaw (3b) is fixed, whereas the upper jaw (3a) slides vertically by means of a guidance system (80).

When the jaws (3a) and (3b) are closed against one another, as represented in FIG. 1A, cavities (5) are formed by virtue of the imprints (4), which are superimposed in pairs.

In the example under consideration, 17 cavities of elongated shape, having a width 1 of approximately 0.5 mm, a length L of approximately 2.5 cm and an approximately circular cross section, which are substantially parallel to one another and evenly spaced out, according to a step p of 1.5 mm, centre to centre, are thus created.

The cavities (5) are closed on the sides and open out to the exterior, on the side where the eyelashes are introduced, via a front opening through which the eyelashes are introduced. The cavities are closed at their rear end.

To use the device (1), the cosmetic composition (6) is, for example, placed in imprints (4) of the part (2b) of the mould (2), mounted on the lower jaw, before introduction of the eyelashes. The composition (6) is a composition as previously described.

The eyelashes are introduced into the imprints (4) of the mould (2) of the device (1) in its open form (FIG. 1B), then the jaws (3a, 3b) are closed so as to hold the eyelashes in the cavities (5).

The heating element (30) brings the composition (6) to a temperature above its melting point, in such a way that the composition (6) takes, in the fluid state, the shape of the imprints (4). The moulding of the composition onto the eyelashes is carried out in situ in the cavities (5) of the mould (2).

Then, the heating element (30) stops heating the composition and said composition is left to cool.

The jaws (3a, 3b) are opened and the eyelashes are withdrawn when the temperature of the composition (6) has come back down below its melting point. The device (1) can be produced such that the closing of the jaws (3a) and (3b) automatically triggers the heating of the composition (6), and so that the heating is automatically stopped when the desired temperature is reached.

The opening of the jaws (3a) and (3b) can take place automatically, as appropriate. As a variant, a sound or light signal can indicate that the jaws can be opened.

Figure 1B:
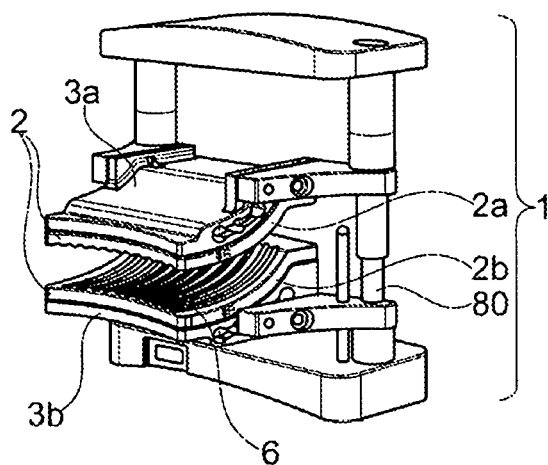
Figure 2:
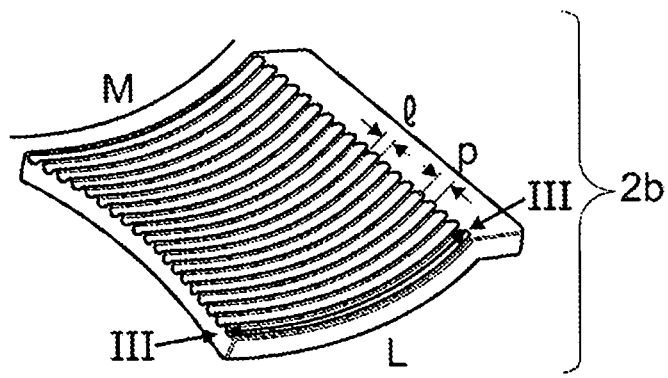
FIG. 2 represents in isolation one of the parts of the mould of FIGS. 1A and 1B.
Figure 3:
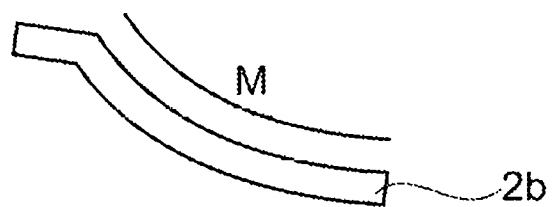
FIG. 3 represents, in section along III of FIG. 2, a part of the mould of this figure.

FIGS. 2 and 3 represent more particularly the part (2b) of the mould (2) of FIGS. 1A and 1B.

It is seen that the part (2b) can be curved along the longitudinal direction M of the imprints (4), in order to reproduce the curved shape of the eyelashes, the radius of curvature preferably being between 15 and 25 mm.

The edge of the part (2b) intended to come into contact with the eyelid may have a rounded shape, concave towards the exterior, with a radius of curvature of preferably between 15 and 25 mm.

The device (1) may, according to one implementation variant of the invention, be in the form of a clamp, as represented in FIGS. 4A and 4B.

Like the device represented in FIGS. 1A and 1B, this device in the form of a clamp comprises a mould (2) in two parts (2a) and (2b). The mould (2) preferably comprises an elastomeric material. The two parts (2a) and (2b) of the mould (2) each have, for example, a thickness e of approximately 2 mm. The two parts (2a) and (2b) of the mould (2) comprise imprints (4), in the form of grooves of elongated shape. The device (1) comprises two jaws (3a) and (3b) which carry respectively the mould parts (2a) and (2b).

Each part (2a, 2b) comprises, for example, 15 imprints (4), for example having a width 1 of approximately 0.5 mm, a length L of approximately 2.5 cm, and a decreasing semicircular cross section so as to give the eyelashes, once moulded with the composition (6), a tapered appearance. The imprints (4) of each part (2a, 2b) of the mould (2) are preferably, as illustrated, substantially parallel to one another. The imprints are evenly spaced out, according to a step p of 1.5 mm, centre to centre.

The mould (2a, 2b) may have a radius of curvature along the direction M of FIG. 4B of between 15 and 25 mm in order to follow the shape of the eyelashes. The edge of the part (2b) intended to come into contact with the eyelid may have a rounded shape, concave towards the exterior, with a radius of curvature of preferably between 15 and 25 mm.

The edge of the jaws (3a, 3b) and of the mould (2a, 2b) intended to come into contact with the eyelid may have a rounded shape, concave towards the exterior, in particular circular, the edge of the eyelid describing, to a first approximation, an arc of a circle.

When the jaws are closed against one another, as represented in FIG. 4A, cavities (5) are formed by virtue of the imprints (4), which are superimposed in pairs. Fifteen cavities (5) of elongated shape, having a width 1 of approximately 0.5 mm, a length L of approximately 2.5 cm and a circular cross section of decreasing diameter as the distance from the opening for introducing the eyelashes increases, which are substantially parallel to one another and evenly spaced out, according to a step p of 1.5 mm, centre to centre, are thus, for example, created. The cavities (5) are closed on the sides and open out to the exterior, on the front side where the eyelashes are introduced, via a circular opening through which the eyelashes are introduced. The cavities are closed at their rear end.

The device (1) in the form of a clamp may comprise, as illustrated, two housings (20a, 20b) into which fingers of one hand, for example the thumb and the index finger, can be introduced so as to move the two jaws (3a, 3b) apart, in order to make it possible to introduce the eyelashes between them and to close them on said eyelashes.

The cosmetic composition (6) to be moulded is placed in imprints (4) of the part (2b) of the mould (2) before introduction of the eyelashes. The composition (6) is a composition as previously described.

An independent oven, not represented, can be used to bring the composition to a temperature above its melting point, before introduction of the eyelashes into the imprints (4) of the mould. The housings (20a, 20b) preferably remain cold, the heating preferably taking place by radiative transfer on the faces of the mould having the imprints.

The cavity of the oven may have a parallelepipedal shape, for example an approximately 10 cm-sided parallelepipedal shape. In addition to its heating function, the oven can also make it possible to present the jaws in such a way that the user can seize them directly between the thumb and index finger, in a single action. In particular, it is possible to use portable clamps of which the internal faces are placed in front of the heat. sources and the external faces bear grasping rings adjusted to the shape of the fingers.

The surfaces carrying the composition can, for example, be heated in the range 30° C.-80° C. The oven can be powered by a low-voltage power source.

The heating temperature can be adjusted by the user. A casing can enable a set temperature to be displayed. The heating power can be about 5 W for example.

When the composition is at a temperature above its melting point, the user's thumb and index finger are introduced into the housings (20a and 20b), then the device (1) is brought into proximity to the eyelashes and the latter are introduced into the imprints (4) of the mould (2) of the device (1) in its open form (FIG. 4B), then the jaws (3a, 3b) are closed so as to hold the eyelashes in the cavities (5).

The moulding is carried out in situ in the cavity or cavities (5) of the mould (2).

The jaws (3a, 3b) are then opened and the eyelashes are withdrawn when the temperature of the composition (6) has come back down below its melting point.

An example of the result of the cosmetic treatment of the eyelashes (7) by such a device (1) is illustrated in FIG. 5.

The device (1) in the form of a clamp may be devoid of a system for guiding the movement of one jaw relative to the other, as represented in FIGS. 6A and 6B. This device has two housings (20a, 20b) for the fingers, like the example previously described.

Only one of the parts can have imprints, which is particularly advantageous for a device (1) devoid of guidance system, since the bringing together of the two parts of the mould does not need to be carried out very accurately.

By way of example, represented in FIG. 7A is a device (1) in which the part (2a) of the mould (2) may be smooth and the part (2b) may comprise semicircular imprints (4).

Moreover, each cavity (5) may have an elongated shape which does not reproduce the curvature of the eyelash(es) introduced, it being possible in particular for the cavity to be non-curved along its longitudinal direction, having, for example, a rectilinear longitudinal axis.

The device (1) in the form of a clamp may comprise a guidance system, for example in the form of reliefs having complementary shapes, which brings the jaws (3a, 3b) into position so that the two parts of the mould (2a, 2b) accurately correspond to one another. The device (1) in the form of a clamp may thus comprise, for example, a male and female cone guidance system.

The device (1) in the form of a clamp may comprise a guidance system of film hinge type or other form of articulation (40), as represented in FIGS. 8A and 8B, such that the jaws can be moved together by a pivoting movement with respect to one another. Each cavity formed by the superimposition of two imprints may have a rectilinear longitudinal axis. The front edges of the jaws (3a, 3b) intended to come into contact with the eyelid may have a circular shape, as illustrated.

During the use of the device (1), the angle a made by the plane of moulding with the horizontal may be zero or non-zero, in particular between 20° and 40°, as illustrated in FIG. 9. Inclining the plane of the moulds makes it possible to fix the curvature of the edge coming into contact with the eyelid as close as possible to the curvature of the eyelid itself.

The hinge (40) may comprise one or more springs (50) as represented in FIG. 10, which assist the opening movement for example.

Figure 11:
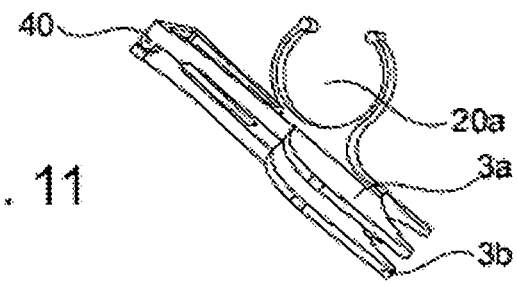

The device (1) in the form of a clamp may comprise a single housing (20a) for receiving a finger, as illustrated in FIG. 11, or two housings, as previously described.

It may be possible for the housing(s) (20a, 20b) to be oriented rotationally, which enables an adjustment according to the angle between the user's thumb and index finger. They may be positionable, where appropriate, at various points (60a), (60b) or (60c), depending on the desired distance between the fingers and the face of the user, as illustrated in FIG. 9.

The mould (2a, 2b) may be integrated into the jaws (3a, 3b). The device (1) in the form of a clamp may then be made of a flexible material of silicone type for example, in order to facilitate demoulding.

The mould may also be made of a flexible material of silicone type with the inclusion of a rigid frame. The housing(s) (20a, 20b) may be made of a rigid material, in order to improve the holding of the clamps in place and the overall shape of the mould, while facilitating demoulding.

It is possible for the mould (2a, 2b) not to be integrated into the jaws (3a, 3b), the jaws carrying the mould, which is then added to the jaws. The mould may be flexible and held on the jaws for example by adherence or by matching shapes, for example by click-fastening and/or sliding attachment. The jaws are then preferably rigid.

The mould (2a, 2b) may or may not be disposable. The jaws (3a, 3b) may or may not be reusable. In particular, the mould (2) is disposable.

The composition (6) may be present within the mould before use of the device (1), in the part (2a), the part (2b) or in both parts, in particular in the form of a pulverulent composition. The loading of the mould with composition may be carried out prior to the use of the device, for example using a metering device.

The device in the form of a clamp has the advantage of being light, of allowing the user to precisely perceive the stresses applied, to the eyelid, during the operations, of creating a very small visual eclipse allowing optimal vision for the user, and of being easy to use.

Figure 12A:
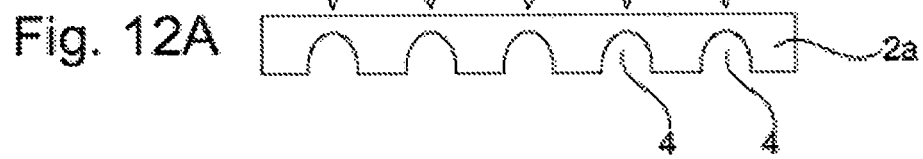
FIGS. 12A and 12B represent various steps for using an example of a demoulding system.
Figure 12B:
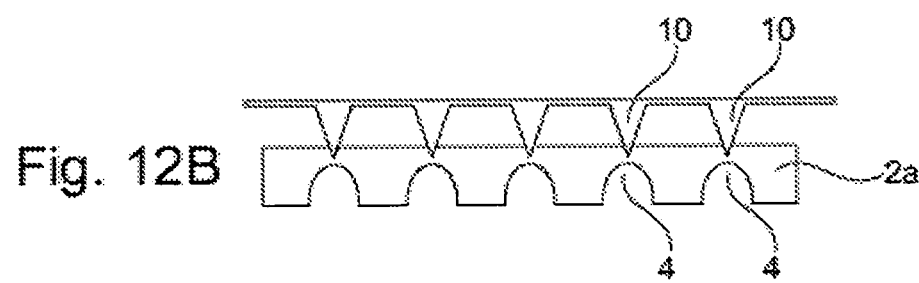

The device (1), whether or not it is in the form of a clamp, may comprise a system which facilitates demoulding, for instance a set of small blades (10) which deform the mould, for example when moved relative to said mould in the direction of the imprints (4), as illustrated in FIGS. 12A and 12B.

Figure 13:
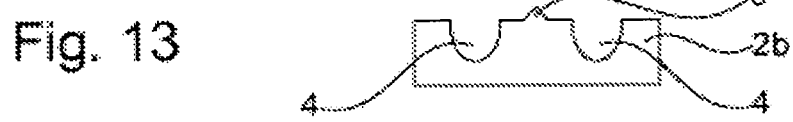
FIG. 13 represents another example of a mould before closing.

The mould (2) may also comprise, as illustrated in FIG. 13, reliefs (9) between two imprints (4) intended to form two cavities, so as to cut any bridges of composition.

Figure 14:
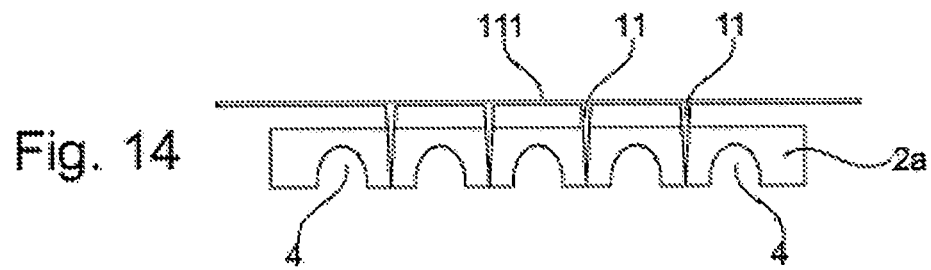
FIG. 14 represents an example of a part of a device equipped with blades.

The device (1) may comprise blades (11) which serve to cut any bridges of composition between two cavities, as illustrated in FIG. 14.

The blades (11) are, for example, retracted within the part of the mould (2a) before closing thereof, and tend to advance upon closing of the mould. The blades (11) are, for example, interlinked with a support (111) which is mobile relative to the part (2a).

As a variant, the material of the part (2a) is elastomeric and overmoulded on the blades (11), which can push on the bridges of composition extending between the imprints (4) by virtue of the deformability of the material with which the part (2a) is made.

Other systems can be further used for cutting the bridges, for example a system which makes it possible to send compressed air via slits located between the imprints or a heating element.

The composition (6) can make it possible to attach an additional fibre (12) to an eyelash (7), with or without axial overlap between the eyelash and the additional fibre, as illustrated respectively in FIGS. 15A and 15B. The eyelash may be on the additional fibre if the additional fibre is in a cavity of the lower mould part, or vice versa, if the additional fibres are in cavities of the upper mould part. In practice, the additional fibres may also be next to the eyelashes depending on the organization caused by the pressure of the two parts of the mould.

The additional fibres may in particular be false eyelashes.

The additional fibres (12) may be placed on hold in the imprints (4) of the mould (2) (FIG. 16A). The composition (6) may then be applied to the ends of the additional fibres

(12) and the eyelashes (7) introduced into the imprints (4) of the mould (2) and brought into contact with the composition (6) (FIG. 16B).

The cavities (5) may, according to various variants, have a shape which is approximately cylindrical (FIGS. 17A and 7B), approximately spherical (FIG. 17D), cylindrical on a part of their length (L) and spherical on the other part of their length (FIG. 17C), or have a decreasing cross section so as to give the eyelash(es), once moulded by the composition, a tapered appearance (FIG. 17B).

They may also have a semi-cylindrical shape in the case where the part (2a) of the mould is flat and the part (2b) of the mould is semi-cylindrical in the cavity (5) formation zone (FIG. 7A).

The depth (j) of the imprints 4 may range between 75 µm and 1.5 mm.

Each cavity (5) can receive one or more eyelashes (7), as illustrated respectively in FIGS. 18A and 18B.

Figure 20:
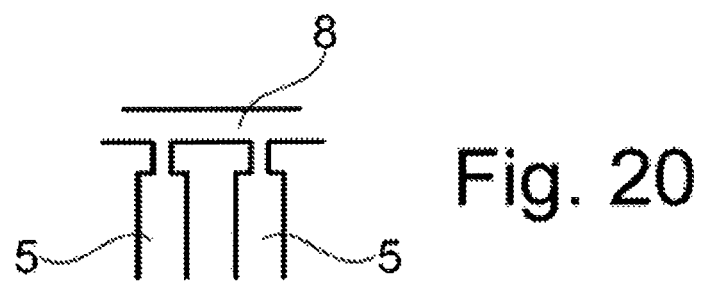
FIG. 20 represents an example of an injection channel communicating with mould cavities.

Before moulding, the composition (6) may, according to various variants, be present on only one part of the cavity (5), as represented in FIGS. 19A to 19C, on all of the cavity, as illustrated in FIG. 19E, or absent from the cavity as represented in FIG. 19D. In the latter case, the composition may be injected via an injection channel (8) communicating with the cavities (5) of the mould, as illustrated in FIG. 20.

The composition (6) may be present initially, before putting the eyelashes in place, on the upper part of the cavity, corresponding to the part (2a) of the mould (FIG. 19A), on the lower part of the cavity, corresponding to the part (2b) of the mould (FIG. 19B), or both on the upper part and on the lower part of the cavity, corresponding to both parts (2a) and (2b) of the mould (FIGS. 19C and 19E).

Figures 21A, 21B:
FIGS. 21A and 21B represent, very diagrammatically, respectively a device according to the invention comprising a heating element and a device according to the invention placed in proximity to a heating element.

The device (1) may comprise, or be placed in proximity to, a heating element (30), as illustrated very diagrammatically respectively in FIGS. 21A and 21B, in order to melt the composition (6), the heating element (30) being, for example, a resistive element, a radiative element or a wave dispenser. The device may provide for the injection of the composition in molten form, in particular via an injection channel (8), as represented in FIG. 20.

Figures 22A, 22B:
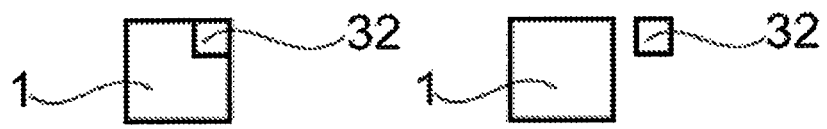
FIGS. 22A and 22B represent, very diagrammatically, respectively a device according to the invention comprising a light element and a device according to the invention placed in proximity to a light element.

The device (1) according to the invention may comprise a triggering system, such as a light element (32), as represented respectively in FIGS. 22A and 22B, for example an IR, UV or visible light illuminator. The mould (2) is then preferably transparent.

EXAMPLES

Example 1: Assembly Containing a Composition Based on a Thermoplastic Polymer and a Device which has a Heating Element 1) Cosmetic Composition A composition in accordance with the invention is prepared as described below.

All the starting materials used are weighed out using a balance (accuracy 0.01 g). The compounds are melted in a jacketed 500 ml heating pan with a circulation of hot oil to control the temperature. The assembly is heated to approximately 95-98° C.

Once the mixture has melted, it is homogenized by stirring using a Moritz blender (stirring of rotor stator type consisting of a fixed part in which a mobile second part rotates at variable speed), in order to disperse the pigments.

The composition is then used hot in liquid form to be deposited on the moulds or at ambient temperature in solid form.

The formulation is prepared using the weight proportions described below.

| Compounds | % by weight (relative to the total weight of the composition) |
|---|---|
| Mixture of copolymer of ethylene-vinyl acetate and of paraffin sold under the name COOL BIND 34-1300 ® by the company National Starch | 90 |
| Iron oxide sold under the name SUNPURO BLACK IRON OXYDE C33-7001 by the company SUN | 10 |

2) Device

The device used in Example 1 is as described in FIGS. 1A and 1B.

It contains two mobile jaws (3a) and (3b), one of the two jaws having a temperature-controlled heating system.

The two parts (2a) and (2b) of the mould, placed between the two jaws, are made of cross-linked silicone elastomer and are 2 mm thick. They each comprise 20 grooves approximately 0.5 mm in diameter over a length of 2.5 cm.

The two jaws comprise two lugs and the two parts of the mould each comprise two housings which fit the lugs.

When the two parts of the mould are brought together, 20 leaktight cavities, closed at their end, are created on the sides.

3) Cosmetic Assembly

The thermoplastic polymer-based molten cosmetic composition is placed in the cavities and grooves of the two parts (2a) and (2b) of the mould using a pipette. The assembly is then left to cool.

The two parts (2a) and (2b) of the mould are then placed on the jaws (3a) and (3b) of the device (1).

The two jaws (3a) and (3b) are moved near to the eyelash fringe and then closed so as to trap it.

The heating is activated by virtue of the heating element of the device (1) for 4 minutes until a temperature of approximately 80° C. is reached within the composition.

The heating is then stopped and the assembly is left to cool for 4 minutes. At the end of the 4 minutes, the two jaws (3a) and (3b) are moved apart.

The two parts (2a) and (2b) of the mould remain attached to the eyelash fringe. The two parts of the mould are therefore moved apart, by pulling along their width, in order to release the eyelashes.

The result is then slightly rubbed in order to break the possible bridges of composition formed between two imprints.

A homogeneous makeup result is obtained on the eyelashes, without any eyelash brushing movement. The makeup is easy to apply without any need to calibrate the amount of composition taken and applied.

The term "homogeneous makeup result" is thus intended to mean, on the one hand, a greater volume by increasing the thickness of the eyelashes and/or increasing the diameter of the eyelashes, and/or an extension of the eyelashes by positioning of sleeves of compositions moulded in the continuity of the free ends of the eyelashes constituting the eyelash fringe.

Example 2: Assembly Containing a Wax-Based Composition and a Device which has a Heating Element 1) Cosmetic Composition A composition in accordance with the invention is prepared as described below.

All the starting materials used are weighed out using a balance (accuracy 0.01 g). The compounds are melted in a jacketed 500 ml heating pan with a circulation of hot oil to control the temperature. The assembly is heated to approximately 95-98° C.

Once the mixture has melted, it is homogenized by stirring using a Moritz blender (stirring of rotor stator type consisting of a fixed part in which a mobile second part rotates at variable speed), in order to disperse the pigments.

The composition is then used hot in liquid form to be deposited on the moulds or at ambient temperature in solid form.

The formulation is prepared using the weight proportions described below.

| Compounds | % by weight (relative to the total weight of the composition) |
|---|---|
| Beeswax sold under the name White Beeswax SP-453P by the company Strahl & Pitsch | 90 |
| Iron oxide sold under the name SUNPURO BLACK IRON OXYDE C33-7001 by the company SUN | 10 |

2) Device

The device used is identical to that of Example 1.

3) Cosmetic Assembly

The wax-based cosmetic composition is placed in the cavities and grooves of the two parts (2a) and (2b) of the mould.

The device and the cosmetic composition are used in the same way as illustrated in Example 1.

A homogeneous makeup result is obtained on the eyelashes, without any eyelash brushing movement. The makeup is easy to apply without any need to calibrate the amount of composition taken and applied.

Example 3: Assembly containing a composition based on a semi-crystalline polymer and a device which has a heating element 1) Cosmetic Composition A composition in accordance with the invention is prepared as described in Example 2.

The formulation is prepared using the weight proportions described below.

| Compounds | % by weight (relative to the total weight of the composition) |
|---|---|
| Poly(C$_{10}$-C$_{30}$)alkyl acrylate sold under the name Intelimer IPA 13-1 NG by the company Air products and Chemical | 85 |
| Iron oxide sold under the name SUNPURO BLACK IRON OXYDE C33-7001 by the company SUN | 15 |

2) Device

The device used is identical to that of Example 1,

3) Cosmetic Assembly

The cosmetic composition based on a semi-crystalline polymer is placed in the cavities and grooves of the two parts (2a) and (2b) of the mould.

The device and the cosmetic composition are used in the same way as illustrated in Example 1.

A homogeneous makeup result is obtained on the eyelashes, without any eyelash brushing movement. The makeup is easy to apply without any need to calibrate the amount of composition taken and applied.

Example 4: Assembly Containing a Composition based on a Thermoplastic Polymer and a Device with no Heating Element 1) Cosmetic Composition A composition as described in Example 1 is prepared.

2) Device

The device used in Example 4 is as described in FIGS. 4A and 4B.

It consists of a clamp containing two mobile jaws (3a) and (3b).

The two parts (2a) and (2b) of the mould, placed between the two jaws, are made of cross-linked silicone elastomer and are 2 mm thick. They each comprise 20 grooves approximately 0.5 mm in diameter over a length of 2.5 cm.

The two jaws comprise two lugs and the two parts of the mould each comprise two housings which fit the lugs.

When the two parts of the mould are brought together, 20 leaktight cavities, closed at their end, are created on the sides.

3) Cosmetic Assembly

The cosmetic composition based on a thermoplastic polymer is placed in the cavities and grooves of the two parts (2a) and (2b) of the mould.

The composition is melted by means of an external heat source.

The assembly is placed in proximity to a heat source, which heats the two parts of the mould.

The oven is based on a heating system comprising high-luminosity 5600 K white LEDs. The LEDs are divided up into 6 networks of 14 LEDs: model Bridgelux BXRA-56C1100-B-00. The total light flux delivered is 8700 lumen. The LEDs produce 124 Lm/W@5600° K. The oven comprises a forced ventilation system with air intakes via the bottom and evacuation holes on the flanks. The LEDs are on a copper heat pipe mounted on a finned radiator, itself cooled by a fan. A parabolic deflector homogenizes the light on the moulds to be heated. The clamp comprises two jaws.

The oven is controlled by a control unit which supplies the oven with a Traco Power 100 W-24 V power supply. It makes it possible to adjust the temperature setting and manages the temperature servo-control. The temperature management is carried out using the ESM-4420 PID (proportional integral derivative) temperature controller.

The assembly makes it possible to produce a heat of approximately 70° C. and rapid heat transfer.

Removed from the oven, the eyelashes are clasped in said assembly which is then cooled for 5 minutes, then demoulded.

The result is then slightly rubbed in order to break the possible bridges of composition formed between two imprints.

A homogeneous makeup result is obtained on the eyelashes, without any eyelash brushing movement. The makeup is easy to apply without any need to calibrate the amount of composition taken and applied.

Example 5: Assembly Containing a Fluid Composition and a Device which has a Heating Element 1) Fluid Cosmetic Composition The fluid cosmetic composition used is identical to that sold under the name Mascara Volume Millions de Cils by the company L'Oréal. This composition has a viscosity of approximately 4 Pa·s.

2) Device

The device used is identical to that of Example 1.

3) Cosmetic Assembly

The cosmetic composition is placed in the cavities and grooves of the two parts (2a) and (2b) of the mould.

The device and the cosmetic composition are used in the same way as illustrated in Example 1.

A homogeneous makeup result is obtained on the eyelashes, without any eyelash brushing movement. The makeup is easy to apply without any need to calibrate the amount of composition taken and applied.

Example 6: Assembly Containing Additional Fibres

The cosmetic composition and the device are the same as those used in Example 1.

Additional fibres 1 cm in length are placed in the imprints of one of the two parts of the mould, as illustrated in FIG. 16A.

The composition is melted and then one drop of the composition is placed, with a hot micropipette, at each end of the additional fibres, as represented in FIG. 16B.

After cooling of the composition, one part of the mould thus prepared is mounted on one jaw and one part of the unused mould is mounted on the other jaw.

The assembly comprising the fibres is heated for 5 minutes in an oven produced as follows.

The oven is based on a heating system comprising high-luminosity 5600K white LEDs. The LEDs are divided up into 6 networks of 14 LEDs: model Bridgelux BXRA-56C1100-B-00. The total light flux delivered is 8700 lumen. The LEDs produce 124 Lm/W@5600° K. The oven comprises a forced ventilation system with air intakes via the bottom and evacuation holes on the flanks. The LEDs are on a copper heat pipe mounted on a finned radiator, itself cooled by a fan. A parabolic deflector homogenizes the light on the moulds to be heated. The clamp comprises two jaws.

The oven is controlled by a control unit which supplies the oven with a Traco Power 100 W-24 V power supply. It makes it possible to adjust the temperature setting and manages the temperature servo-control. The temperature management is carried out using the ESM-4420 PID (proportional integral derivative) temperature controller.

The assembly makes it possible to produce a heat of approximately 70° C. and rapid heat transfer.

Removed from the oven, the eyelashes are clasped in said assembly which is then cooled for 5 minutes, then demoulded.

The additional fibres are attached to the eyelashes and the connection is aesthetic.

An attachment without overlap is obtained, as illustrated in FIG. 15B.

Example 7: Assembly Containing Additional Fibres

The cosmetic composition and the device are the same as those used in Example 1.

Additional fibres 1 cm in length are placed in the imprints of one of the two parts of the mould, as illustrated in FIG. 16A.

The composition is melted and then one drop of the composition is placed, with a hot micropipette, at each end of the additional fibres, as represented in FIG. 16B.

After cooling of the composition, one part of the mould thus prepared is mounted on one jaw and one part of the unused mould is mounted on the other jaw.

Before clasping the eyelashes, the jaws and the mould are heated for 5 minutes.

The eyelashes are then clamped and the assembly is heated for 2 minutes.

The assembly is left to cool for 5 minutes, then demoulded.

The additional fibres are attached to the eyelashes and the connection is aesthetic.

An attachment with overlap is obtained, as illustrated in FIG. 15A. Indeed, the preheating melts each of the small drops of composition and, in doing so, allows the eyelashes to advance towards the additional fibres.

Example 8: Assembly Containing Additional Fibres

A device identical to that of Example 1 is produced, with the difference that the elastomeric mould comprises, in addition to the grooves, a groove which is 1 mm deep across a width of 4 mm and transverse to the length of the mould. The transverse groove is produced 5 mm from the edge.

Additional fibres are, as in Example 7, placed in the grooves. The meltable composition, as described in Example 1, is placed in the transverse groove, then the whole thing is heated in order to melt the composition, and then left to cool.

While cooling, the material traps the additional fibres along the width of the groove. The melted then cooled composition is mainly on the part of the additional fibres facing the transverse groove. There is also a small amount of melted then cooled composition along the length of the additional fibres (along a length of approximately 5 mm).

Finally, a jaw-comprising heating system as described in Example 7 is used to weld the additional fibres to the existing eyelashes.

The invention claimed is:

1. Cosmetic assembly configured to treat keratin fibres, comprising:
    a cosmetic composition having a melting point of between 40° C. and 120° C., and comprising at least 15% by weight of meltable compound(s), relative to a total weight of the cosmetic composition; and
    a device comprising a mould, the mould comprising at least two cavities, into each of which at least one of said fibres can be at least partially introduced for the purposes of moulding said cosmetic composition onto at least one part of said fibre(s) present in the at least two cavities,
    wherein the at least two cavities are formed by bringing two jaws together and each cavity delimits a space which is closed with the exception of one end via which said fibre(s) that are at least partially introduced into said cavity communicate with the exterior.

2. Assembly according to claim 1, wherein the cosmetic composition has a melting point of between 40° C. and 100° C.

3. Assembly according to claim 1, wherein the cosmetic composition is chosen such that, when said composition is heated to a temperature Tc, a ratio of the heat consumed between −20° C. and Tc by the composition to a total heat consumed Δh between −20° C. and 120° C. is greater than 0.4.

4. Assembly according to claim 1, wherein the meltable compound(s) is (are) chosen from thermoplastic polymers, waxes, semi-crystalline polymers, and mixtures thereof.

5. Assembly according to claim 1, wherein the cosmetic composition has a solids content of greater than or equal to 42% by weight, relative to the total weight of the composition, said composition being fluid or solid at 25° C. and at 1 atm.

6. Assembly according to claim 1, wherein the cosmetic composition is solid and in that it comprises from 40% to 100% by weight of meltable compound(s), relative to the total weight of the composition.

7. Assembly according to claim 1, wherein the cosmetic composition is fluid and comprises from 15% to 60% by weight of meltable compound(s), relative to the total weight of the composition.

8. Assembly according to claim 1, wherein the cosmetic composition also comprises at least one colorant.

9. Assembly according to claim 1, wherein the cosmetic composition comprises less than 20% of volatile solvent(s).

10. Assembly according to claim 1, wherein the cosmetic composition is aqueous or anhydrous.

11. Assembly according to claim 1, wherein the device comprises at least one heating element which serves to increase a temperature of the cosmetic composition, the increase in the temperature inducing a change of state of the composition.

12. Assembly according to claim 1, wherein the device comprises at least one system for admitting material, which serves to introduce a part or all of the cosmetic composition into the mould cavities.

13. Assembly according to claim 11, wherein the heating element is at least one light element or microwave element, which serves to increase the temperature of the cosmetic composition.

14. Assembly according to claim 1, wherein the mould is disposable.

15. Assembly according to claim 1, wherein the device comprises one or more additional fibres, the cosmetic composition ensuring the attachment of the additional fibre(s) to the keratin fibre(s), with or without axial overlap between the two types of fibres.

16. Assembly according to claim 1, each cavity constituting a space which is substantially entirely closed, in an absence of keratin fibre.

17. Process for cosmetic treatment of one or more keratin fibres using the cosmetic assembly of claim 1, comprising onto at least one part of said fibres in the at least two cavities of the device.

18. Process according to claim 17, wherein said fibres are, optionally individually, at least partially introduced into said cavities.

19. Process according to claim 17, wherein the cosmetic composition is brought to a temperature greater than or equal to its melting point.

20. Process according to claim 17, wherein the cavities of the mould are formed by bringing together two jaws.

21. Process according to claim 17, wherein the cosmetic composition is moulded onto at least one part of at least one of said keratin fibres and of at least one additional fibre, the cosmetic composition ensuring attachment of the additional fibre(s) to the keratin fibre(s), with or without axial overlap between the two types of fibres.

22. Assembly according to claim 1, wherein the keratin fibres are eyelashes.

23. Assembly according to claim 1, wherein the cosmetic assembly is configured to heat said cosmetic composition to a temperature sufficient to allow moulding of the composition onto at least one part of said fibre(s) but without risk of burning an individual to whom the at least one part of said fibre(s) belong at a time of moulding.

* * * * *